(12) United States Patent
Kuiper et al.

(10) Patent No.: US 6,945,944 B2
(45) Date of Patent: Sep. 20, 2005

(54) THERAPEUTIC LIMB COVERING USING HYDROSTATIC PRESSURE

(75) Inventors: Hendrik Klaas Kuiper, Edwards, MS (US); Bobby E. Reed, Vicksburg, MS (US); Danny Earl Ellis, Utica, MS (US)

(73) Assignee: Incappe, LLC, Brandon, MI (US)

( * ) Notice: Subject to any disclaimer, the term of this patent is extended or adjusted under 35 U.S.C. 154(b) by 69 days.

(21) Appl. No.: 10/114,103

(22) Filed: Apr. 1, 2002

(65) Prior Publication Data

US 2003/0191420 A1 Oct. 9, 2003

(51) Int. Cl.$^7$ ................................................. A61F 5/00
(52) U.S. Cl. .............................. 602/13; 602/5; 602/27; 602/62; 602/65; 128/882; 128/DIG. 20; 2/22; 2/911
(58) Field of Search ........................... 602/2, 5, 12, 13, 602/14, 21, 23, 27, 62, 65, 66, 78; 128/876, 882, 898, DIG. 20, 64, 80; 601/148–152; 2/22, 911, 919, DIG. 3

(56) References Cited

U.S. PATENT DOCUMENTS

| | | |
|---|---|---|
| 26,663 A | 1/1860 | French |
| 267,435 A | 11/1882 | Leiter |
| 1,117,168 A | 11/1914 | Crowley |
| 1,199,914 A | 10/1916 | Mossor |
| 1,608,239 A | 11/1926 | Rosett |
| 1,629,108 A | 5/1927 | Lake |
| 1,732,380 A | 10/1929 | Sarason |
| 2,272,481 A | 2/1942 | Rinkes et al. |
| 2,531,074 A | 11/1950 | Miller |
| 2,657,385 A | 11/1953 | Cushman et al. |
| 2,694,395 A | 11/1954 | Brown |
| 2,832,336 A | 4/1958 | Davis et al. |
| 3,083,708 A | 4/1963 | Gottfried |
| 3,086,529 A | 4/1963 | Munz et al. |
| 3,153,413 A | 10/1964 | Gottfried |
| 3,164,152 A | 1/1965 | Nicoll |
| 3,177,866 A | 4/1965 | Wesslund |
| 3,186,404 A | 6/1965 | Gardner |

(Continued)

FOREIGN PATENT DOCUMENTS

| | | |
|---|---|---|
| CA | 960537 | 1/1975 |
| DE | 1 491 215 | 6/1969 |
| EP | 0 039 629 A1 | 4/1981 |
| EP | 0 169 874 B1 | 10/1989 |
| EP | 0 388 200 B1 | 9/1994 |
| EP | 0 552 515 B1 | 5/1999 |
| FR | 2 481 109 | 10/1981 |
| GB | 483111 | 4/1938 |
| GB | 1171361 | 11/1969 |
| GB | 2350798 A | 12/2000 |
| SU | 574213 | 9/1977 |
| WO | WO 98/25568 A1 | 6/1998 |
| WO | WO 98/48759 A1 | 11/1998 |
| WO | WO 01/93797 A2 | 12/2001 |

*Primary Examiner*—Henry Bennett
*Assistant Examiner*—Andrea M. Ragonese
(74) *Attorney, Agent, or Firm*—Kirkpatrick & Lockhart Nicholson Graham LLP

(57) ABSTRACT

The present invention provides a therapeutic limb covering and an associated method of treating chronic swelling of a limb. The limb covering is uses hydrostatic pressure provided by liquid contained within the covering to apply pressure to the limb. The limb covering comprises a substantially non-distensible flexible outer layer, a distensible flexible inner layer joined together and a liquid tight bladder therebetween. The covering may be adapted for releasable securement about a limb such as an arm or a lower leg and foot of a patient. After placement on the limb, when the bladder is filled with a liquid, such as water, it expands to contact and apply pressure to the limb.

12 Claims, 25 Drawing Sheets

U.S. PATENT DOCUMENTS

| | | |
|---|---|---|
| 3,351,055 A | 11/1967 | Gottfried |
| 3,403,673 A | 10/1968 | MacLeod |
| 3,548,809 A | 12/1970 | Conti |
| 3,683,897 A | 8/1972 | Shield et al. |
| 3,786,805 A | 1/1974 | Tourin |
| RE27,957 E | 4/1974 | Larson |
| 3,824,992 A | 7/1974 | Nicholson et al. |
| 3,955,565 A | 5/1976 | Johnson, Jr. |
| 3,977,396 A | 8/1976 | Cartier |
| 4,013,069 A | 3/1977 | Hasty |
| 4,029,087 A | 6/1977 | Dye et al. |
| 4,149,529 A | 4/1979 | Copeland et al. |
| 4,206,751 A | 6/1980 | Schneider |
| 4,266,298 A | 5/1981 | Graziano |
| 4,320,746 A | 3/1982 | Arkans et al. |
| 4,374,518 A | 2/1983 | Villanueva |
| 4,378,009 A | 3/1983 | Rowley et al. |
| 4,402,312 A | 9/1983 | Villari et al. |
| 4,502,470 A | 3/1985 | Kiser et al. |
| 4,590,925 A | 5/1986 | Dillon |
| 4,628,945 A | 12/1986 | Johnson, Jr. |
| 4,648,392 A | 3/1987 | Cartier et al. |
| 4,722,332 A | 2/1988 | Saggers |
| 4,762,121 A | 8/1988 | Shienfeld |
| 4,805,601 A | 2/1989 | Eischen, Sr. |
| 4,914,753 A | 4/1990 | Chang |
| 4,938,208 A | 7/1990 | Dye |
| 4,941,458 A | 7/1990 | Taheri |
| 4,945,905 A | 8/1990 | Dye et al. |
| 4,977,891 A | 12/1990 | Grim |
| 4,989,589 A | 2/1991 | Pekanmäki et al. |
| 5,036,838 A | 8/1991 | Sherman |
| 5,060,641 A | 10/1991 | Jones |
| 5,063,910 A | 11/1991 | Cartier |
| 5,092,317 A | 3/1992 | Zelikovski |
| 5,139,475 A * | 8/1992 | Robicsek ............. 602/13 |
| 5,170,783 A | 12/1992 | Smith |
| 5,218,954 A | 6/1993 | van Bemmelen |
| 5,279,545 A * | 1/1994 | Reese, Sr. ............ 602/21 |
| 5,288,286 A * | 2/1994 | Davis ............... 602/6 |
| 5,324,318 A | 6/1994 | Smith |
| 5,328,445 A | 7/1994 | Spahn et al. |
| 5,378,223 A * | 1/1995 | Grim et al. ............ 602/6 |
| 5,403,265 A | 4/1995 | Berguer et al. |
| 5,435,009 A | 7/1995 | Schild et al. |
| 5,450,858 A | 9/1995 | Zablotsky et al. |
| 5,464,385 A * | 11/1995 | Grim ............... 602/27 |
| 5,489,259 A * | 2/1996 | Jacobs et al. ......... 602/13 |
| 5,524,292 A | 6/1996 | Hargens |
| 5,588,954 A | 12/1996 | Ribando et al. |
| 5,591,200 A | 1/1997 | Cone et al. |
| 5,626,556 A | 5/1997 | Tobler et al. |
| 5,688,225 A | 11/1997 | Walker |
| 5,711,760 A | 1/1998 | Ibrahim et al. |
| 5,717,996 A | 2/1998 | Feldmann |
| 5,759,164 A | 6/1998 | Pacey |
| 5,795,312 A | 8/1998 | Dye |
| 5,833,639 A * | 11/1998 | Nunes et al. ......... 602/23 |
| 5,868,690 A | 2/1999 | Eischen, Sr. |
| 5,916,183 A | 6/1999 | Reid |
| 6,001,119 A | 12/1999 | Hampson et al. |
| 6,066,107 A | 5/2000 | Habermeyer |
| 6,080,120 A | 6/2000 | Sandman et al. |
| 6,228,044 B1 | 5/2001 | Jensen et al. |
| 6,315,745 B1 | 11/2001 | Kloecker |
| 6,358,219 B1 * | 3/2002 | Arkans ............. 601/152 |
| 6,485,447 B1 * | 11/2002 | Lavery et al. ......... 602/23 |
| 6,641,549 B2 * | 11/2003 | Darcey ............. 602/8 |

\* cited by examiner

THERAPEUTIC LIMB COVERING USING HYDROSTATIC PRESSURE

FIELD OF THE INVENTION

The present invention relates to devices and methods for the treatment of chronic swelling.

BACKGROUND OF THE INVENTION

Chronic swelling of a limb is a medical condition that results in pain, tissue breakdown and immobility for many patients. Such swelling is often caused by venous insufficiency or other disease such as lymphedema. In the case of venous insufficiency or venous stasis, the venous system of the extremities, particularly the lower extremities, experiences reduced blood flow. The reduced blood flow results from venous dysfunction in the extremity that limits the effective return of blood from the extremity back to the heart. The problem is exacerbated in lower extremities due to the effect of gravity, which must be overcome to move the blood back to the heart. However the arms are also susceptible to chronic swelling conditions such as may be caused by cancer of the lymph glands or post-mastectomy radiation treatment.

A common treatment for chronic swelling is the application of external pressure to increase tissue pressure in the region. This treatment decreases the swelling and improves tissue oxygenation, thereby allowing tissue to heal. In applying pressure to the leg, it is desirable to apply the highest pressure at the ankle and gradually decrease the pressure that is applied toward the top of the lower leg. However applying pressure to the limb can be problematic for a patient that also suffers from poor arterial perfusion. Poor arterial perfusion is caused by insufficient blood supply and blood has difficulty reaching the limb, not just returning from the limb as with venous insufficiency. Applying pressure to the limb serves to help prevent blood from ever reaching the limb. Therefore, traditional methods of treating chronic swelling cannot be used for patients with poor arterial perfusion.

A known means for applying pressure to the limb to treat chronic swelling is highly elastic bandages or multiple wrappings (in the case of devices for the foot and leg). The wrapping is wrapped tightly around the limb to apply pressure for the purpose described above. The wrappings generally must be applied by a caregiver. After initial treatment, elastic stockings are used by the patient to continue preventative treatment. The stockings do not need to be wrapped about the limb, however, they must be stretched over the limb, including the foot, ankle and calf in order to be donned. A disadvantage of these devices is that they are difficult for a user, particularly an elderly or disabled user, to stretch onto the limb for suitable therapeutic benefit. Also, the wrappings and elastic stockings constantly apply pressure to the limb when they are worn without a mechanism for selectively discontinuing the pressure they apply. Thus patients that also suffer from poor arterial perfusion cannot use the wrappings and stockings because there is no way for them to periodically discontinue the pressure to allow blood to flow to the limb.

Another approach to treatment of chronic swelling has been to apply pressure to the limb with a fluid. An advantage of using a fluid to apply pressure is that it readily conforms to the unique contours of a limb and can be applied easily by a user. U.S. Pat. No. 4,805,601 (Eischen) and U.S. Pat. No. 5,711,760 (Ibrahim et al.) disclose lower limb coverings having air bladders for applying pneumatic pressure to the limb. Other pressure applying devices use the pressure applied by a liquid surrounding the limb. U.S. Pat. No. 3,977,396 (Cartier) discloses an apparatus using liquid pressure, which comprises a tub filled with liquid mercury into which the patient places the limb surrounded by an impervious flexible wrapping to prevent contact with the mercury. The pressure applied by the liquid mercury around the surfaces of the submerged limb is believed to provide treatment for the chronic swelling condition of the limb.

Another treatment device described in U.S. Pat. No. 5,759,164 (Pacey) uses hydrostatic pressure applied to the limb by a liquid tight bag wrapped around the limb and filled with liquid. The flexible bag is filled with liquid to apply pressure to the limb by a separate liquid reservoir that is attached to the body above the limb and joined to the bag by a conduit

SUMMARY OF THE INVENTION

The present invention provides a therapeutic limb covering that uses hydrostatic pressure applied to a limb to treat chronic swelling. The limb covering comprises a flexible, substantially non-distensible outer layer and joined to a flexible, distensible inner layer and defining a liquid tight bladder therebetween. The bladder defined between the layers is filled with liquid, such as water, to create the hydrostatic pressure that is applied to the limb when the covering is worn.

The covering is shaped to fit relatively closely to the limb. For example, in a device intended for the lower leg and foot, the covering is configured similar to a boot having a foot portion and a calf portion extending substantially perpendicular to the foot portion. However, the device alternatively may be configured to fit about an arm. The covering circumferentially surrounds the limb to apply pressure to a substantial portion of the limb surface. The covering may have a securable opening, secured by means such as Velcro® hook and loop fasteners to facilitate donning by the patient. Velcro® fasteners provide for a wide range of size adjustability useful for fitting different sized limbs. Alternatively, the opening may be secured by a zipper or other means such as snaps, buckles or ties. With such fasteners, size adjusters, such as Velcro® hook and loop fasteners straps, may additionally be employed on the limb covering to take up slack between the covering and the limb to achieve a snug, but not tight, fit with the limb. Regardless of the fastening means used, adjustability for a snug fit permits a single limb covering size to properly fit a range of limb sizes. Additionally, achieving a snug fit reduces the amount of liquid that is needed to in the bladder to apply the necessary hydrostatic pressure to effectively counter the chronic swelling. Reducing the amount of liquid required to use the limb covering reduces the weight of the covering, which is important in maintaining the mobility of the patient.

In one aspect of the invention the limb covering is configured to include one or more structural supports to help maintain axial fortitude of the covering and promote uniform coverage of the device over the limb. The support may be joined to the outer layer of the covering for at least a portion of its expanse. Column strength of the covering material is important to prevent collapse of the covering under the weight of the liquid contained in the bladder. Resistance to collapse ensures that the covering retains the intended coverage area of the limb and the appropriate column height of the liquid. However, the structural support should be configured to permit some lateral flexibility to permit movement of the limb and mobility of the patient.

In one embodiment of the covering, the structural support comprises a layer of semi-rigid material such as polymer closed-cell foam. The structural layer of foam is secured to the outer layer and extends over a substantial portion of its inner or outer surface to provide longitudinal consistent compressive strength throughout the structure to maintain the form of the covering. In addition to the benefit in strength, the foam structural layer provides other desirable properties to the boot additional to its performance as a structural support. First, the foam layer provides insulation from physical shock to the limb, such as may occur if a fixed object is bumped by the limb during movement. If a shock is experienced by the limb, the foam layer provides some padding to cushion the impact. The foam layer also provides some thermal insulation to the limb. The cell structure of the foam serves to reduce heat loss through the layer thereby helping to keep warm the limb wrapped by the covering. The thermal insulative effect of the foam, in conjunction with a reduction of evaporation when polymer layers are used for the wrapping, may tend to promote healing of any wounds present on the limb while the device is worn. Additionally, the liquid used to fill the bladder can be warmed to any comfortable temperature to warm the limb and the liquid jacket further serves to help prevent heat loss. The liquid jacket also helps to protect the limb from shock, absorbing impacts with other objects.

In another aspect of the invention the covering is configured such that the bladder extends through the boot-type covering from the underside of the foot to at least the mid-portion of the calf. The arrangement of the bladder under the foot causes alternating compression and release of the bladder during ambulation of the patient. Each compression of the bladder creates a sudden increase in pressure transmitted as a wave throughout the bladder in the liquid contained therein. The wave transmitted through the liquid creates circulation of the liquid in the bladder. The pressure wave causes movement of the bladder wall against the limb surface that mimics the calf muscle pump to urge movement of blood or collected fluids upward from the limb.

The configuration of the covering uses the principle of pressure exerted by a liquid column to the therapeutic benefit of the limb experiencing chronic swelling. The column of liquid maintained around the limb by the covering provides hydrostatic pressure directed inwardly toward the limb that increases linearly from the upper portion of the limb covering downward to the bottom portion of the covering. Due to the effect of gravity, the amount of pressure exerted by liquid in the bladder at any given point is dependent on the height of the liquid above that point. In the example of a covering configured as a boot to cover the foot and lower leg, the liquid column maintained therein applies the greatest outward pressure at the lowest region of the boot, which corresponds to the foot, ankle and lower calf. As the boot extends upward on the calf, pressure exerted by the liquid decreases linearly due to the influence of gravity on the liquid column. However, if needed, pressure applied by the limb covering can be increased beyond what is provided solely by the force of liquid maintained in a column around the limb. A "pre-charge" pressure can be created in the limb covering to increase the magnitude of pressure that is applied by the liquid column at every point across the limb. The pressure can be increased by increasing the amount of liquid transferred into the bladder to increase pressure above that which would be exerted by hydrostatic pressure alone. The pre-charge pressure also can be created by reducing the available volume of the covering by tightening its fit around the limb after it has be filled and the port sealed.

The pressure properties of the liquid column maintained by the covering correspond to the therapeutic requirements of the limb. The lowest portion of the limb requires the greatest pressure from the covering due to the influence of gravity on the blood in the venous network that is not returning properly to the heart. Consequently, for effective treatment, higher pressure should be applied to the limb in lower regions to counter the increased swelling that occurs there.

The limb covering according to the present invention exhibits theses desirable performance characteristics naturally due to the pressure distribution exhibited by a liquid column. When a limb with the therapeutic covering is maintained such that the longitudinal axis of the limb is maintained vertically, the liquid column applies greater pressure at the lower regions of the limb where it is most needed. For example, in the case of a boot covering, the longitudinal axis of the limb is considered to be oriented vertically when the longitudinal axis of the calf is vertical, such as when standing. However, pressure around the lower region of the limb can be easily discontinued by elevating the limb so that the longitudinal axis this placed in a horizontal position. In the horizontal position, most of the liquid column is no longer above the lower region of the limb and pressure is greatly reduced. This capability of the limb covering makes it suitable for use by patients with poor arterial perfusion. Those patients are able to discontinue pressure applied by the covering from time to time simply by elevating their limb to a horizontal position.

It is an objective of the present invention to provide a therapeutic limb covering that is lightweight and easily donned and used by a patient.

It is another object of the invention to provide therapeutic limb covering that provides hydrostatic pressure against the surface of the limb to provide therapeutic benefit to the limb.

It is another object of the invention to provide a therapeutic limb covering that comprises a substantially non-distensible outer layer, a distensible inner layer and a liquid tight bladder between them.

It is another object of the invention to provide a therapeutic limb covering that comprises a substantially inelastic shell joined to an elastic double-walled bladder.

It is another object to provide therapeutic limb covering that comprises a bladder that extends under the foot and upward along the calf so that ambulation tends to compress the bladder to create alternating pressurization of the bladder.

It is another object of the invention to provide a therapeutic limb covering using hydrostatic pressure that employs at least one structural support to help maintain the shape and form of the covering.

It is another object of the invention to provide a therapeutic limb covering that provides thermal and shock insulation to the limb it covers.

It is another object of the invention to provide a therapeutic limb covering that is configured to fit a wide range of limb sizes.

It is another object of the invention to provide a method of treating chronic swelling using hydrostatic pressure.

It is another object of the present invention to provide a therapeutic limb covering to treat chronic swelling that also can be safely used by patients with poor arterial perfusion.

BRIEF DESCRIPTION OF THE DRAWINGS

The foregoing and other objects and advantages of the invention will be appreciated more fully from the following further description thereof, with reference to the accompanying diagrammatic drawings wherein.

DESCRIPTION OF THE ILLUSTRATIVE EMBODIMENTS

Figure 1:
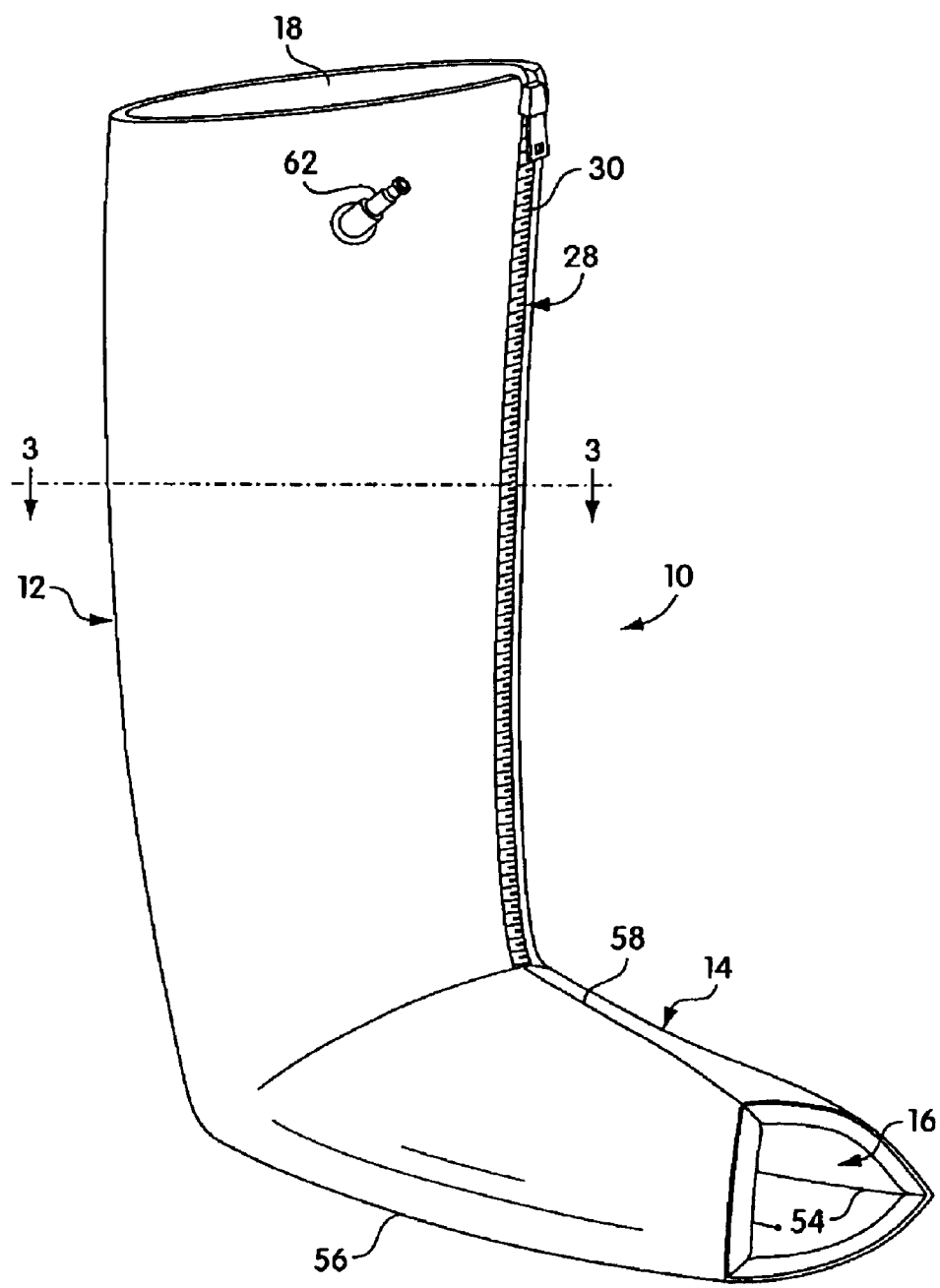
FIG. 1 is a side view of a therapeutic limb covering.
Figure 2:
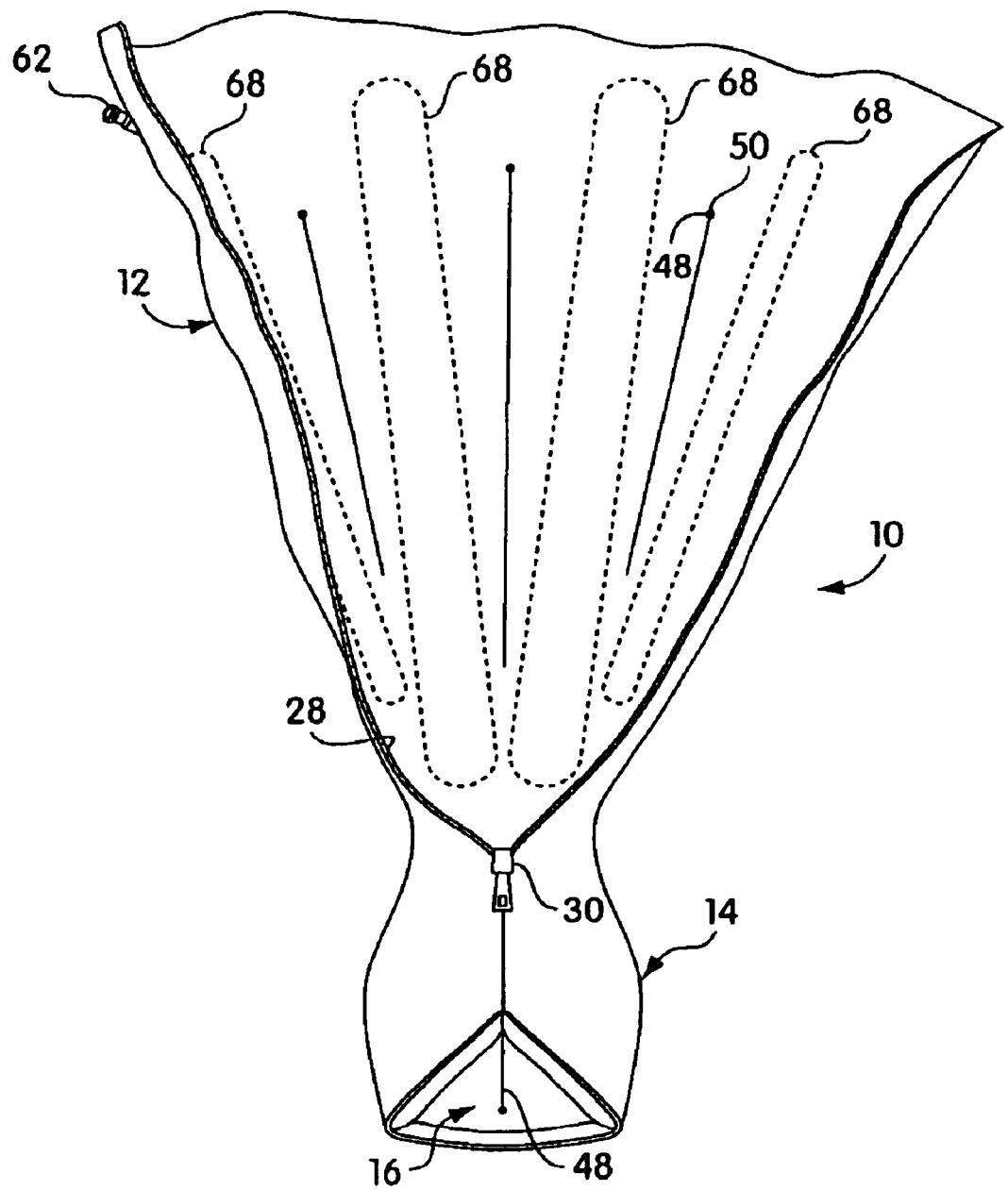
FIG. 2 is a front view of a therapeutic limb covering.
Figure 4:
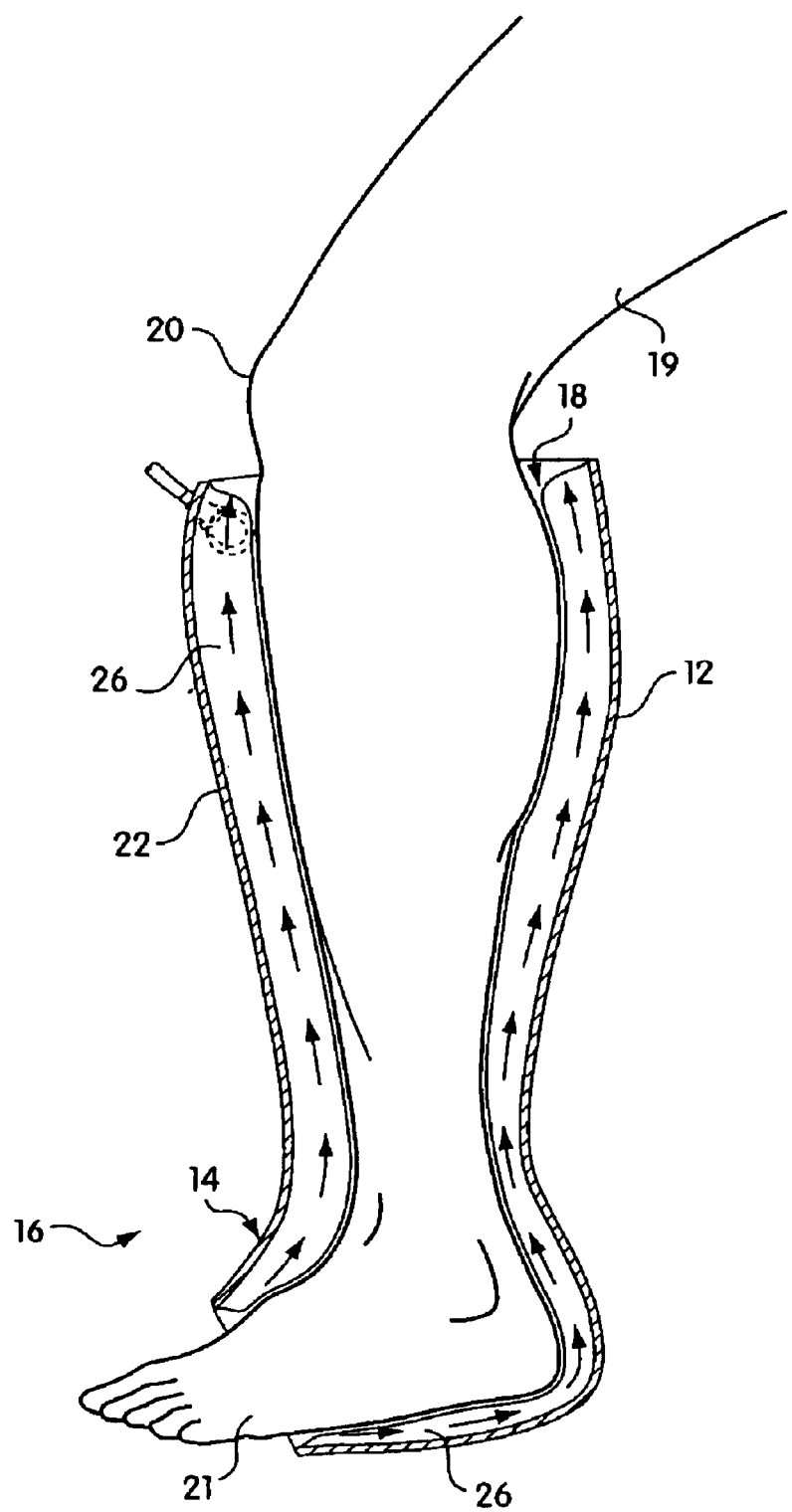
FIG. 4 is an illustration of a therapeutic limb covering being worn about the lower leg and foot of a user showing movement of liquid contained in the covering.

FIGS. 1 and 2 show a therapeutic limb covering according to the present invention. FIG. 1 shows a limb covering configured as a boot 10 configured to fit about a patient's foot and lower leg. The boot comprises a calf portion 12 and a foot portion 14. The covering is donned about a patient's foot and lower leg such that the toes protrude from toe opening 16, and the calf portion 12 extends up the lower leg such that calf opening 18 is positioned just below a patient's knee 20 (as best seen in FIG. 4). The foot portion 14 is oriented substantially perpendicular to the calf portion 12 to mimic the orientation of the foot and leg under most circumstances, but the entire covering is made from flexible materials so that the orientation between the foot and leg remains flexible and capable of movement.

Figure 3:
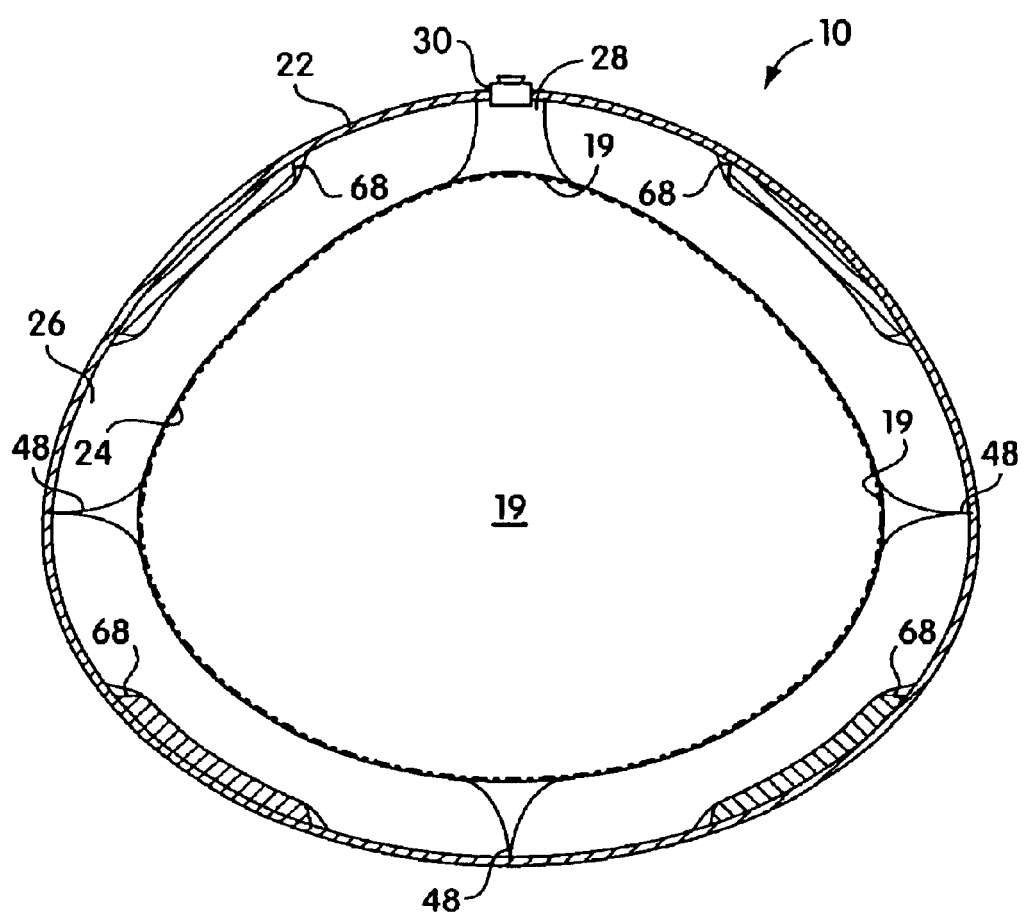
FIG. 3 is a sectional view of the therapeutic limb covering of FIG. 1 taken along the section line 3—3 of FIG. 1.

FIG. 3 is a sectional view of the boot shown in FIG. 1 taken along the line 3—3 of FIG. 1. The limb covering comprises a flexible but substantially non-distensible outer layer 22 joined to a flexible and distensible inner layer 24 to define a liquid tight bladder 26 therebetween. The bladder is filled with any convenient liquid, such as water, to apply pressure to the limb 19 about which the covering is worn. It is noted that other suitable liquids may have densities that are different than water to provide a different resulting pressure such include salt water or gel substances.

The distensible inner layer is elastic and expands under the pressure of the liquid in the bladder, while the inelastic outer layer 22 retains the shape of the covering so that it remains properly positioned around the limb. Liquid transfer valve 62, bonded to the calf portion 12 and in liquid communication with the bladder 26 provides sealable port through which liquid may be added to or removed from the bladder.

The covering is provided with an opening 28 that is releasably securable by means such as a zipper 30 so that the covering may be opened to facilitate donning by the patient then secured to place the covering close proximity to the surface of the patient's limb. The opening may be located on the front of the calf portion 12, longitudinally extending the length of the calf portion. Alternatively, the opening 28 may be positioned elsewhere on the calf, such as on the side of the calf portion 12, which is shown in FIG. 7.

Figure 7:
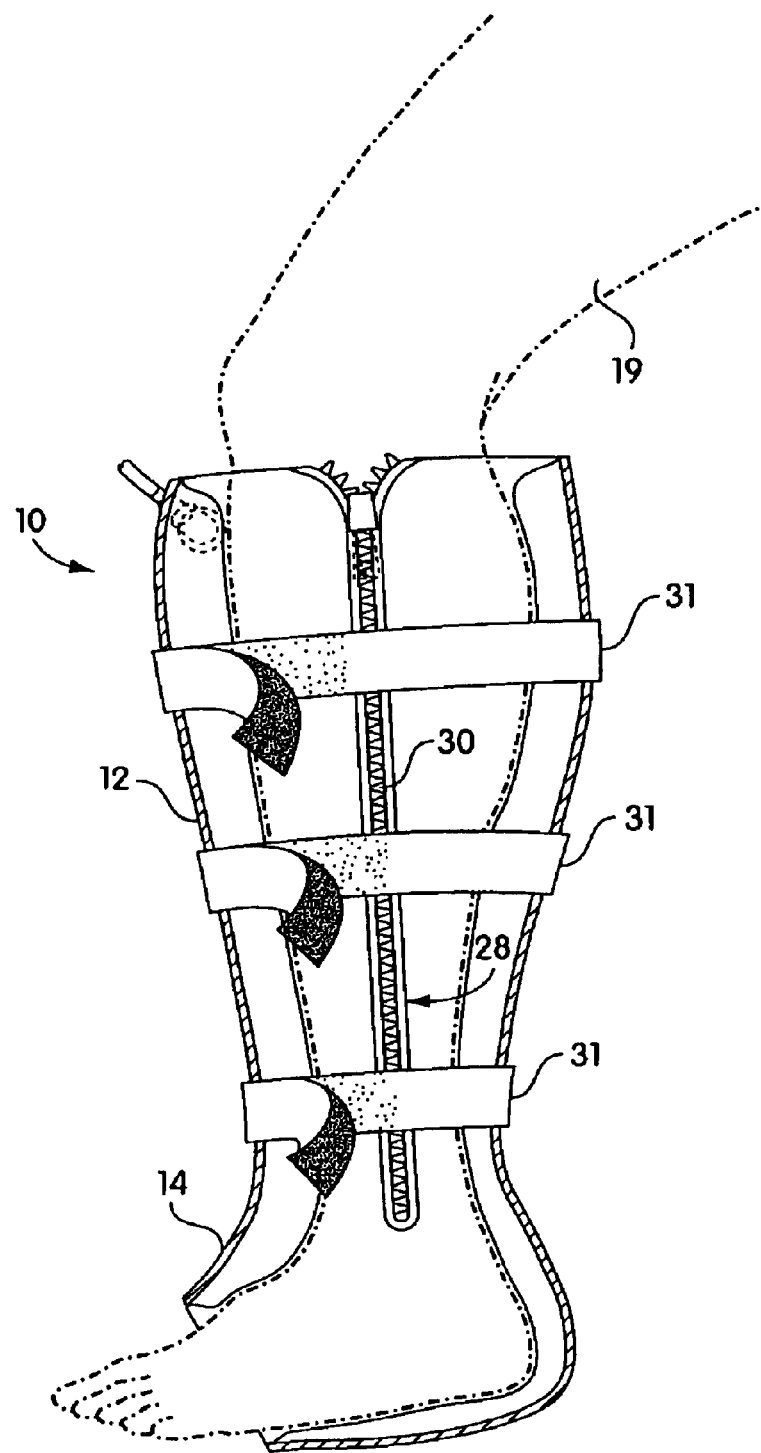
FIG. 7 is a transparent side view of a therapeutic limb covering with a side mounted securement mechanism.

Additionally, as shown in FIG. 7 size adjusters 31 may be employed at various locations on the covering to tighten or loosen its fit about a limb and to accommodate a variety of limb sizes. The size adjusters 31 may comprise easily securable means such as Velcro straps, ties or buckles placed around the calf and/or foot portions, capable of cinching the covering close to the limb after the opening 28 is closed, if needed. The size adjusters make a single size of limb covering useable for a variety of limb sizes. Different sizes of limb coverings may need to be provided for extreme size differences, but it is expected that approximately three size ranges (small, medium and large) would be sufficient to fit the majority of the adult population. Additionally the size adjusters provide a means for adjusting the tightness of the covering about the limb in order to control the volume of the bladder. Tightening a limb covering that is already filled with water will create an "over-fill condition" where the amount of liquid in the bladder exceeds the available non-distended volume of the bladder. That condition increases the magnitude of pressure applied by the limb covering against the limb. Alternatively, tightening an unfilled boot against the limb will reduce the amount of liquid required to fill the bladder and establish the liquid column about the limb, which reduces weight.

A dynamic feature of the boot limb covering is modulation of the hydrostatic pressure that occurs during movement, which is illustrated in FIG. 4. During ambulation, when the patient puts weight on the limb 19, the foot 21 compresses the bladder 26, reducing its volume and forcing liquid outward and upward from the area. A sudden movement of liquid from beneath the foot 21 causes a positive pressure wave that travels upward through the limb covering as illustrated by pressure wave arrows 86. The upwardly traveling pressure wave 86 externally mimics the pumping action of muscles in the leg to provide an additional therapeutic benefit in the treatment of chronic swelling of the limb. The pressure wave modulates the hydrostatic pressure in the bladder, which serves to distend the inner layer 24 in a wavelike fashion. That action of the inner surface against the skin surface of the limb 19 urges blood to flow up the leg to help treat chronic swelling of the limb.

Figure 5:
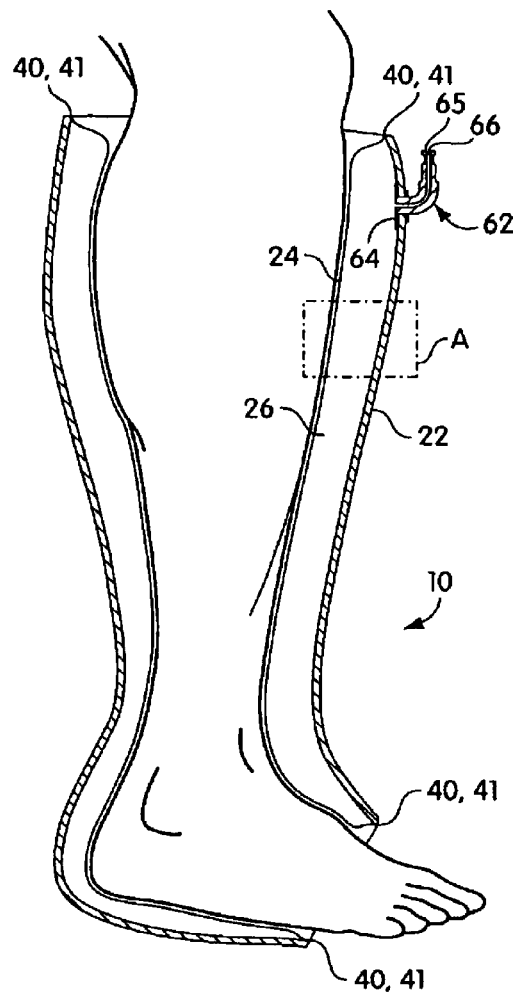
FIG. 5 is a sectional side view of a therapeutic limb covering.

FIG. 5 shows a sectional view of a limb covering configured as a boot 10 having outer and inner layers 22 and 24 and a bladder 26 defined between the layers. Area A is shown in detail in FIG. 5A to illustrate the composition of the layers. The outer layer 22 should be flexible yet substantially non-distensible and liquid tight. To achieve this combination of characteristics, the outer layer may be comprised of an outer shell 32 to provide inelasticity. Possible materials include GORE-TEX® fabric or KEVLAR®, nylon, polyester, denim, acetate or thick PVC, neoprene or natural rubber.

Figure 5A:
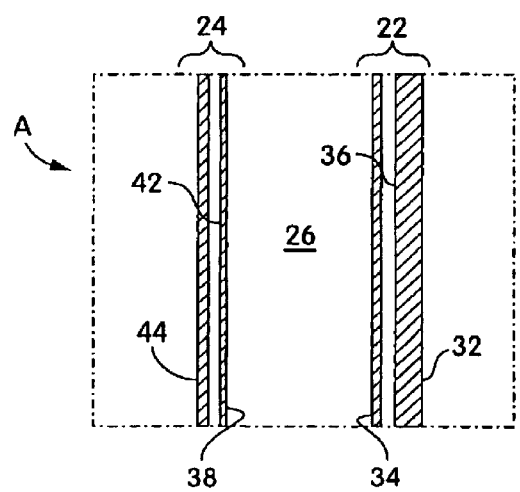
FIG. 5A is a detail of area A of FIG. 5.

If the material of the shell is not liquid tight, a liquid tight backing 34 may be bonded to the inside surface 36 of the shell 32. The backing is bonded to the inside surface 36 of the shell to ensure that the shell will be impermeable to liquid contained within the bladder 26. In FIG. 5A, the backing 34 is shown separated from the shell 32 for illustration purposes only, but it should be understood that the backing is bonded directly to the shell at least at its outer peripheral edge 40 and preferably across its entire surface. The backing may be any liquid tight flexible material such as PVC of a thickness on the order of approximately 6 mil, or other thicknesses necessary to handle expected pressures. Also other materials such as polyurethane may be used. It should be understood that bonding of the materials together may be accomplished by means such as radiofrequency (RF) welding, adhesive bonding, heat welding, ultra sonic welding, stitching or any other suitable means of bonding the materials.

The inner layer 24 should be flexible, elastic and distensible to communicate to the limb the pressure created by the liquid. The inner layer may be constructed of a liquid tight, thin, flexible bladder wall 38 that is bonded to outer layer 22 at least around their peripheral edges 40, 41. The outside surface 42 of the inner layer, which faces the limb, may contact the limb directly or may be lined with a comfortable material liner 44 to contact the patient's skin. The liner may be formed from any flexible material that will not interfere with the elasticity of the bladder wall 38. A possible liner material choice is polyester. The liner should be bonded to at least the outer periphery 41 of the bladder wall but may be bonded across selected portions or all of its surface area, but should not degrade the distensibility of the bladder wall. Alternatively, the comfortable material suggested for the liner 44 may be worn separately on the limb, such as a stocking, before donning of the limb covering. The exemplary materials listed above for layer construction of the therapeutic limb covering are intended only to be illustrative and should not be considered to limit the scope of the invention. Other suitable materials meeting the objectives described for the inner and outer layers may be used.

Figure 6:
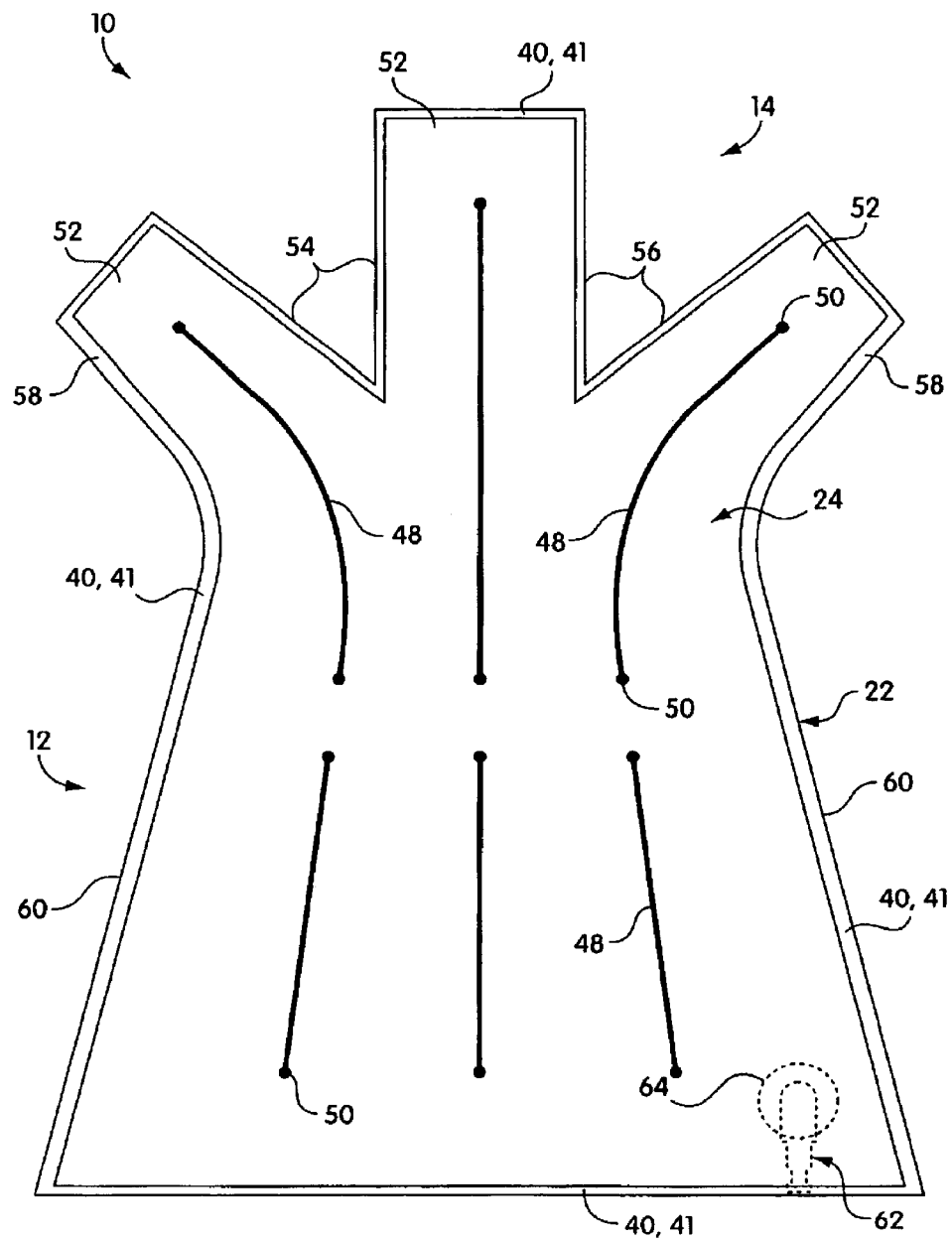
FIG. 6 is a top view of a pattern for the therapeutic limb covering.

FIG. 6 shows an illustrative configuration for a pattern from which the boot type therapeutic limb covering may be constructed. FIG. 6 shows the inner layer 24 bonded on top of the outer layer 22 prior to final bonding of the pattern edges to create the finished boot. The inner layer 24 is bonded to the outer layer 22 along their outer peripheries 40, 41. Additionally, the inner layer 24 may be bonded to the outer layer 22 at selected locations such as along surface seams 48 to help promote integrity of the liquid bladder 26 that is defined between the inner and outer layers 24 and 22. Surface seams 48 need only be a thin line of bonding and may have circular termination points 50 to distribute separation forces created by the liquid, thereby adding to the integrity of the seam.

The foot region 14 of the boot is shown to have three trunk portions 52 while the covering is in the flat sheet pattern form. The trunk portions are bonded together to form the foot portion 14 shown in FIGS. 1 and 2. To join the trunk portions, two left foot seams 54, two right foot seams 56 and two top seams 58 are bonded to form a foot portion 14. The calf portion 12 of the boot is left unbonded at calf seam 60 to provide an opening that will have attached to it a securable closure device such as a zipper. All bonds between the layers described in connection with the limb covering may be created by known techniques for the given materials such as RF welding, adhesive bonding or heat welding, ultrasonic welding or stitching.

Also shown in FIG. 6, in phantom, is the liquid transfer valve 62 joined to the calf portion 12 of the boot 10. The liquid transfer valve permits liquid to be added or removed from the bladder defined between inner and outer layers 24 and 22. The liquid transfer valve protrudes from and is accessible from the outer layer 22 but penetrates through the layer to be in fluid communication with the bladder 26 (as shown in FIG. 5). The valve 62 is held in place through the outer layer by a valve flange 64 bonded to the backing 34 and inside surface 36 of the shell 32 to be liquid tight. Inner valve mechanism 66 may be spring loaded to be easily opened by the user by applying attachment pressure with a liquid supply line to the valve's nipple 65. Removing the supply line permits the spring-loaded valve to close and contain the ¢liquid. A suitable valve mechanism as described above, is known as a luer-lock and is available from ARKPLAS Products, Inc., Flippin, Ark. An angled valve connector, part number 167ACU, available from Halkey Roberts Corp., St. Petersburg, Fla., may also be used. Alternatively, a conventional luer fitting with a manually controlled valve may be used to permit exchange of liquid into the bladder of the covering and to seal the liquid within the bladder.

At least one structural support member 68 may be provided in the calf portion 12 of the limb covering as shown in FIGS. 2 and 3. The structural support members provide support to the covering, in the calf region 12 so that the covering does not collapse under the weight of liquid maintained in a vertical column against the leg. Though the inelastic outer layer 22 provides support to keep the shape of the covering when filled with liquid, the structural support members provide additional fortitude to reduce the chance of sagging and to help maintain the shape of the covering. The structural support members should be axially stiff to provide column strength to the covering yet be laterally flexible, to bend, flex and conform to the leg during ambulation of the patient. Any rigid lightweight polymer is a suitable material for the structural members. Any number of members may be used. However, four to six rectangular shaped members extending the majority of the length of the calf region 12 of the boot 10 is believed to provide sufficient support to the covering.

The structural support members may be joined to the inside surface 36 of the outer shell 32 by bonding and may be covered by the liquid proof backing 34 that is also bonded to the inside surface 36 of the shell. As shown in FIGS. 2 and 3, the structural supports should be positioned between surface seams 48, which serve to join the inner layer 24 to the outer layer 22 along selected regions. Because the structural support members are thin, light weight and are joined to the outer layer 22, the patient does not feel them and they do not interfere with filling of the bladder 26. It is noted that other configurations for the structural support members and mounting locations, including mounting on the exterior surface of the outer layer 22, may be used.

In another configuration of the covering, structural support may be provided to the covering by a single rigid member, bonded to or incorporated into the outer layer, either internally or externally. The single member may have a plurality of vertically extending grooves to form a plurality of corresponding ribs therebetween. The thicker material of the ribs helps to provide column strength in the member and the covering. The grooves provide lateral flexibility for bending of the covering during patient movement.

Figure 8:
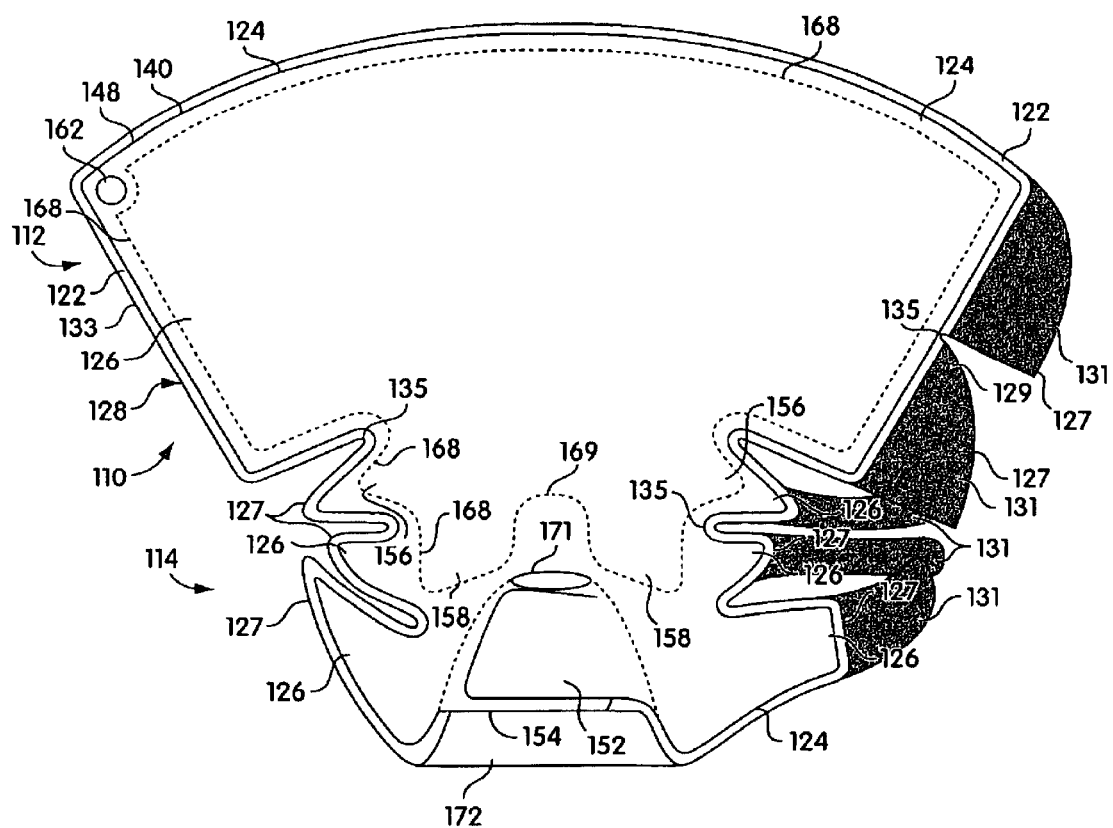
FIG. 8 is a front view of an embodiment of the therapeutic limb covering in an open configuration.
Figure 9:
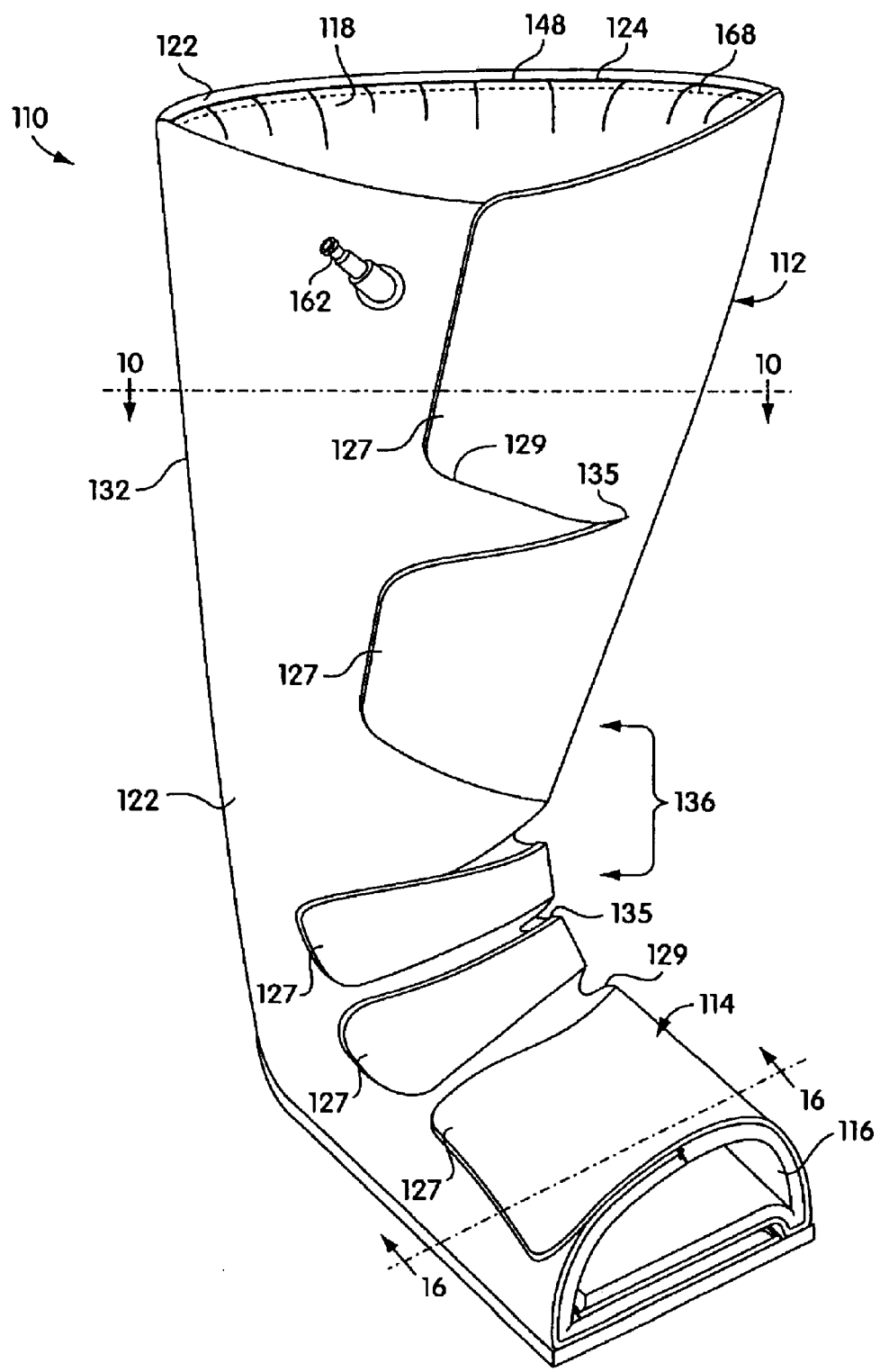
FIG. 9 is a front, isometric view of an embodiment of the therapeutic limb covering in a closed configuration.

Another embodiment of the limb covering is shown in FIGS. 8 and 9. The boot covering 110 is similar to the boot embodiment 10 discussed in connection with FIGS. 1–7 above, but employs several alternate configurations that may be employed altogether as in the example discussed here or may be employed individually in a covering as desired by one practicing the invention. The covering 110 is similar in that it is formed from a substantially inelastic outer layer 122 and an elastic inner layer 124 bonded together at their peripheries to define a liquid tight bladder 126 between them. The resulting covering can be formed into a shape to cover the limb to be treated. In particular, the covering may be formed as a boot 110 for the foot and lower leg, or may be formed as a sleeve to be fitted over the arm as will be discussed below. In the case of the boot, a calf portion 112 and foot portion 114 are formed as well as corresponding calf and toe openings 118 and 116. The boot 110 also has a securable opening 128 to facilitate donning by a patient.

An alternate feature shown on boot 110 is the system for securing the opening 128. A securement mechanism 130 may be comprised solely of Velcro type closures rather than the zipper 30 of boot 10 shown in FIG. 1. A Velcro securement mechanism also eliminates the need for additional, separate size adjuster components described above in connection with boot 10. In the alternate configuration shown in boot 110, Velcro hook portions 131 may be joined to several flap areas 127 formed along an edge 129 of the opening 128. The hook portions may be joined to the outer layer of the boot by bonding techniques known in the art such as stitching or RF welding. A suitable hook fastener is the Hook 88 fastener, part number 184150 available from Velcro USA Inc, Manchester, N.H. Corresponding Velcro loop portions (not shown) may be fitted to the opposing edge 133 of the opening 128. Alternatively, the outer layer 122 may comprise a shell 132 of a material that provides a suitable napped surface with closed loops capable of catching the Velcro hook portions. In this configuration, the entire outer surface of the covering is available to secure the Velcro hook portions thereby providing a wide range of adjustability to accommodate different sized limbs. Additionally, the napped texture of the outer shell provides a comfortable feeling to the touch of the user. A suitable shell material for serving as the loop portion fastener is an engageable knit loop fabric such as part number S040 available from Highland Industries Inc., Framingham, Mass.

The several flaps 127 formed into the outer layer 122 of the covering permit greater flexibility through the ankle area of the foot when the covering is secured around a limb. The articulated shape of the covering provided by the flaps reduces the amount of excess material that may tend to bunch up and bulge when flexing occurs at the ankle area. However, the triangle shaped flaps 127 still provides adequate coverage of the limb by the bladder 126 through the area of the ankle and foot as the bladder is shaped to extend along the articulated flap, at least partially. When the flaps 127 are wrapped around the limb and secured, substantial coverage of the limb by the bladder extending along the flaps occurs. The flaps are defined as cut-outs in the outer layer 122 and have rounded termination points 135 that reduce stresses on the material that may lead to tearing during use.

Figure 10:
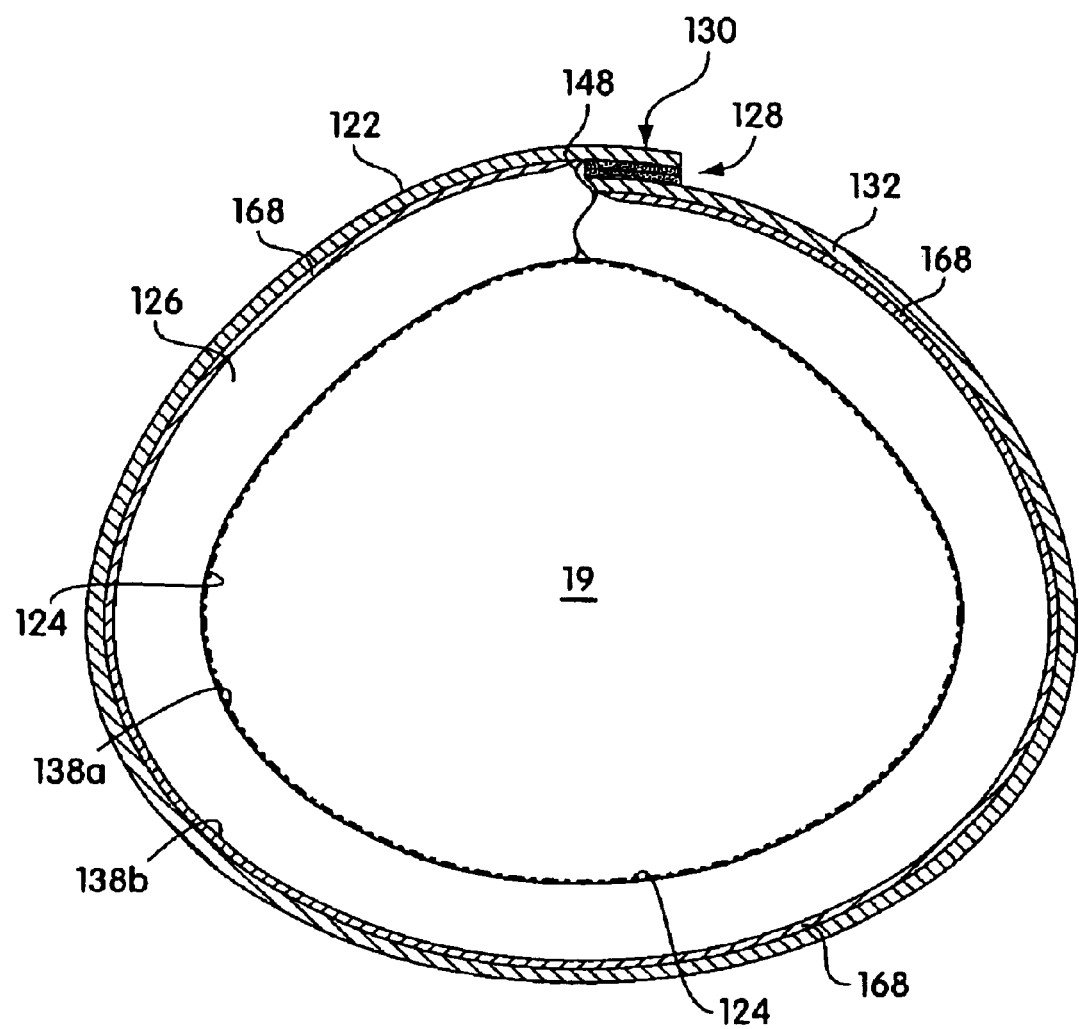
FIG. 10 is a sectional top view of an embodiment of the therapeutic limb covering taken along the line 10—10 of FIG. 9.
Figure 10A:
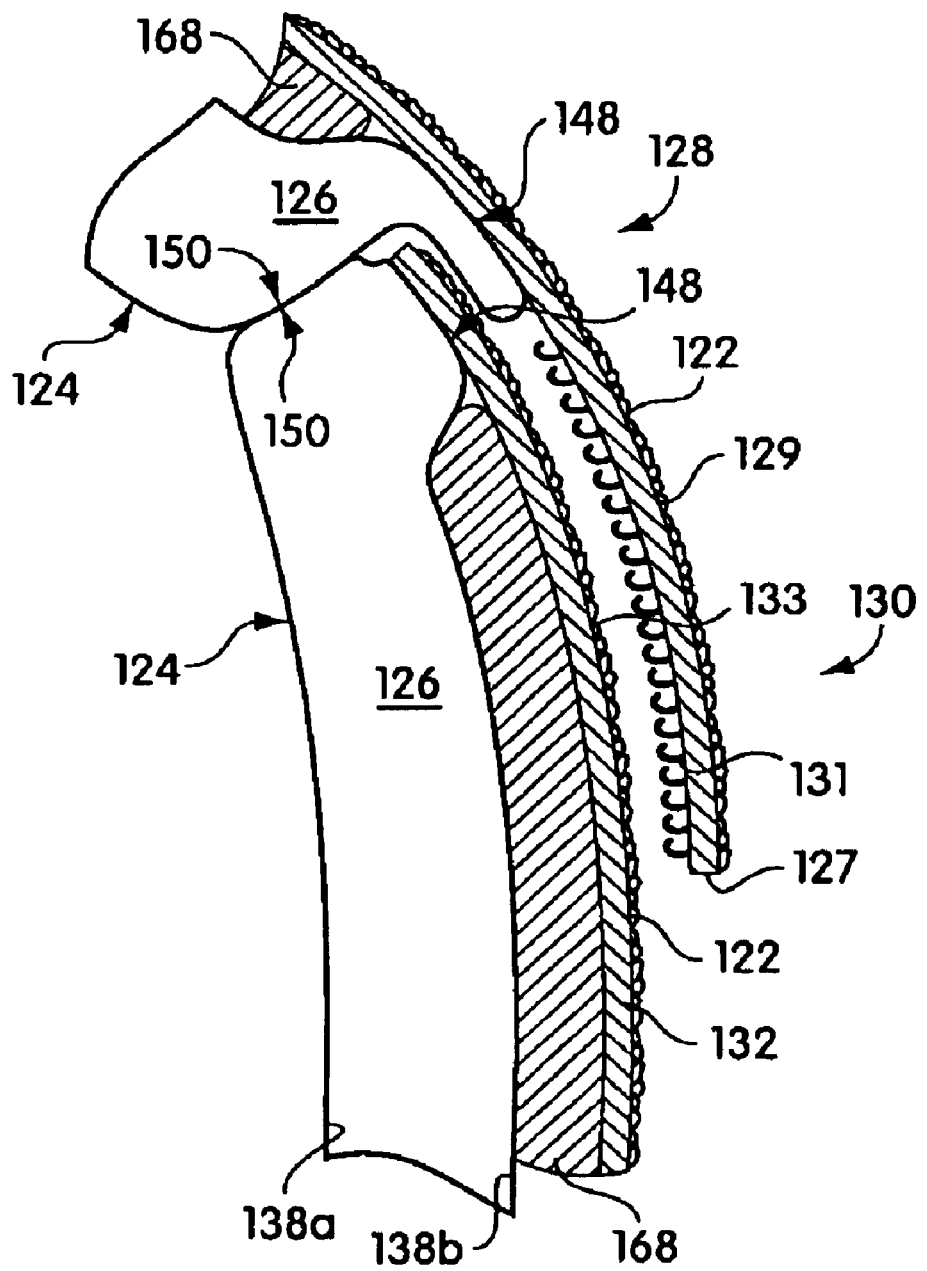
FIG. 10A is a detailed view of the opening area of the therapeutic limb covering as shown in FIG. 10.

Another alternate configuration as shown in the covering of FIGS. 8 and 9 is a continuous, open bladder 126. The bladder 126 is configured as an independent, double-walled continuous chamber, without segmented areas or baffles as was defined by surface seams 48 in the therapeutic limb covering 10 embodiment shown in FIGS. 1–7. A continuous bonding seam 148 around the periphery 140 of the bladder is present to join the two walls of the bladder together. The bladder is bonded to the to the shell 132 of the outer layer 122 around the periphery 140 of the bladder at seam 148. The several surface seams 48 of the previous embodiment are not employed. The resulting bladder 126 provides a more continuous contact with the limb 19 as is best shown in the cross-sectional illustration of FIG. 10 taken along the line 10—10 of FIG. 9. As compared with the same cross-sectional view of the previous embodiment shown in FIG. 3, improved contact by the inner layer 124 with the limb 19 is promoted around the entire circumference of the limb in the absence of surface seams 48. In FIG. 10, the only minor discontinuity of contact between the inner layer 124 and the limb 19 occurs at the area of the opening 128, which is secured by securement mechanism 130. At this juncture, the ends of the bladder 150, defined by periphery seams 148 define the only discontinuity in contact of the bladder 126 with the limb 19. However, this discontinuity is minimized by sizing the boot such that the bladder end points 150 at least abut each other when the covering is wrapped closed around the limb, as shown in FIG. 10. This configuration should occur when the maximum sized limb is inserted into a limb covering of a given size range. This size of limb covering will also be able to accommodate smaller limb diameters as the opening 128 can be overlapped, such that the bladder ends 150 overlap to make the closed diameter of the covering tighter to achieve a snug fit about the smaller sized limb. The overlap configuration of the secured limb covering is not shown in the figures but should be readily recognized by those skilled in the art. The more complete limb contact provided by the continuous chamber 126 is believed to maximize the therapeutic benefit provided by the covering. FIG. 10A shows in detail, the connection interfaced between the opposing edges 129 and 133 of the opening 128 of the covering. It can be seen that the ends of the bladder 150 meet in abutment when the securement mechanism 130 of Velcro hooks 131 is joined to shell 132 of the outer wall of the outer layer of the covering.

Another alternative configuration incorporated into the covering 110 is a single piece structural support member 168 (shown in phantom in FIGS. 8 and 9) that is incorporated with the covering as a layer, extending substantially coextensive with the shell 132 of the outer layer 122. The structural support member 168 is a flexible, but semi-rigid material that provides longitudinal compressive strength to prevent buckling of the covering under weight of the liquid, yet it allows lateral flexibility for bending of the limb. A suitable material for the single piece structural support member 168 may be a polymer foam material, such as NBR/PBC elastomeric foam, a closed cell foam material, available under the trade name ENSOLITE© available from Rubatex, Roanoke, Va. A structural support layer 168 formed from such material may be on the order of approximately ⅛" to ¼" in thickness. As shown in FIG. 8 and in FIGS. 11, 13 and 14 to be discussed in detail below, the structural support 168 should extend over a substantial portion of at least the calf portion 112 of the limb covering 110, which will experience the majority of the compressive loading under the weight of the liquid contained in the bladder while the covering is in use. For example, as shown in the figures, the structural support 168 may extend substantially coextensively with the shell 132 of the outer layer 122, down to the bottom of the calf portion 112, but need not extend into the foot portion 114. Rather, the base of the structural support 168 may terminate near the sole 172 of the covering. An arch 169 may be formed in the structural support around the top of the heel to permit flexibility of the covering in this area and to reduce chaffing on the heel during ambulation and to facilitate donning of a shoe over the device. Additionally, an aperture 171 may be formed in the outer layer 122 at the heel to provide additional flexibility in the heel region.

The structural support should be joined to the outer wall 122 of the covering to best provide support and strength for maintaining the form of the covering when filled with liquid. The support may be joined to the interior surface of the shell 132 of the outer layer 122 and be covered by the bladder wall so as not to be exposed to liquid contained in the bladder. The structural support may be joined to the outer layer 122 by bonding at certain points or across its entire surface to the shell 132. Alternatively, the structural support may be captured in close proximity to the shell 132 by the bladder wall that is bonded around its periphery 140 to the shell 132. Capturing the structural support member 168 between the shell and bladder does not require bonding of the support member directly to the shell 132, yet maintains the support in sufficiently close proximity to the shell so as to provide fortification to the outer layer and covering.

Figure 11:
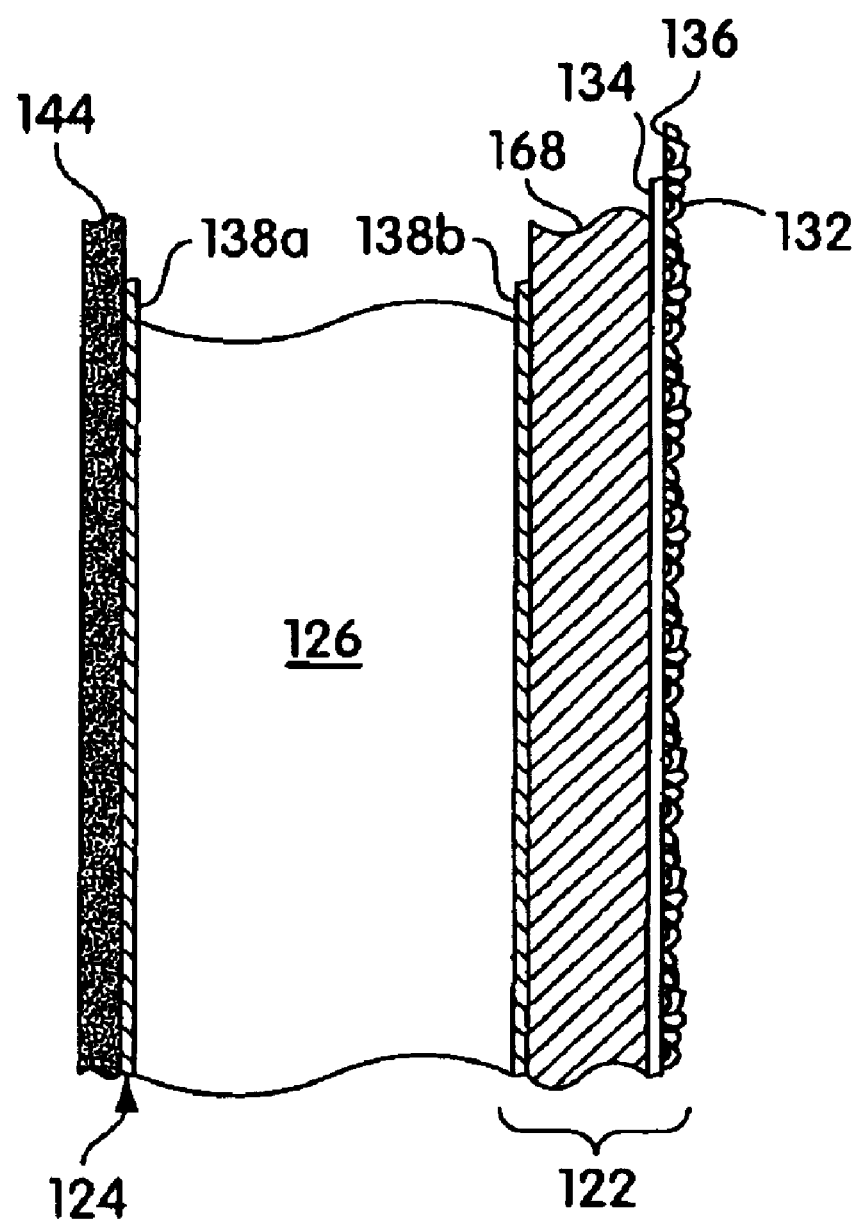
FIG. 11 is a detailed view of the arrangement of layers in the therapeutic covering.

FIG. 11 shows a detail of the arrangement of layers that form the covering 110 shown in FIGS. 8–10A. As shown in FIG. 11, the outer layer 122 may be considered as comprising all layers arranged external to the liquid held in the bladder 126. The inner layer 124 may be considered as comprising all layers positioned internal of the liquid held in the bladder: between the user's limb and the liquid. Thus, the outer layer 122, at its outermost surface, comprises a shell 132 that is flexible and may serve as a loop portion of a Velcro fastener. A suggested material for achieving this purpose is an engageable knit loop fabric as discussed above. On the inside surface 136 of the shell 132, a polyurethane coating 134 is applied as a backing material. Next, a structural support member 168, such as a polymer foam material may be adhered or bonded directly to the inside surface 136 of the shell 132, or may be captured against the shell 132 by a wall 138b of the bladder. The bladder 126 is a self-contained unit comprising two walls 138a and 138b with the interior of the bladder 126 defined therebetween. As a self-contained unit, the bladder walls 138a and 138b are bonded to each other around their peripheries 140 (not shown in FIG. 11). When incorporated into the covering, the bladder is bonded to the inside surface 136 of the shell, continuously along the outer peripheries 140 of the bladder walls along seam 148. A suitable material for the double wall bladder is a polyurethane film, on the order of approximately 0.008" in thickness. A suitable film is available under the trade name Duraflex under part no. PT9200US/Natural available from Deerfield Urethane, Deerfield, Mass. The bladder may be joined to the shell 132 by any of the bonding techniques mentioned above in connection with the first embodiment, such as RF welding, sonic welding, adhesive or chemical bonding or stitching.

In comparison with the first embodiment, discussed in connection with FIGS. 1–7, and in consideration of the premise that layers on the patient side of the liquid comprise the inner layer, the single inner wall 138a of the bladder may be considered to represent the inner layer 124 in the covering embodiment 110. The resulting combination of layers provides a substantially non-distensible outer layer 122 and a distensible inner layer 124, with a liquid tight bladder 126 therebetween. The covering embodiment 110 may also be defined as comprising an inelastic shell 132 joined to an elastic double wall bladder with a structural support member captured between the shell and bladder.

Optionally, a soft material 144 may be provided as a liner over the inner layer 124 defined by bladder wall 138 to provide for a more comfortable surface that will be in contact with the skin of the user. A soft material 144 should cover the entire surface of the inner layer 124 and may be joined to the covering by adhesive, bonding, or stitching to the outer layer 122. Alternatively, the cloth liner 144 may be implemented as a stocking that is worn over the limb separately, donned prior to placing on the covering 110. The liner 144 should be of a material that does not interfere with the distensibility of the inner layer 124 during use.

Figure 12:
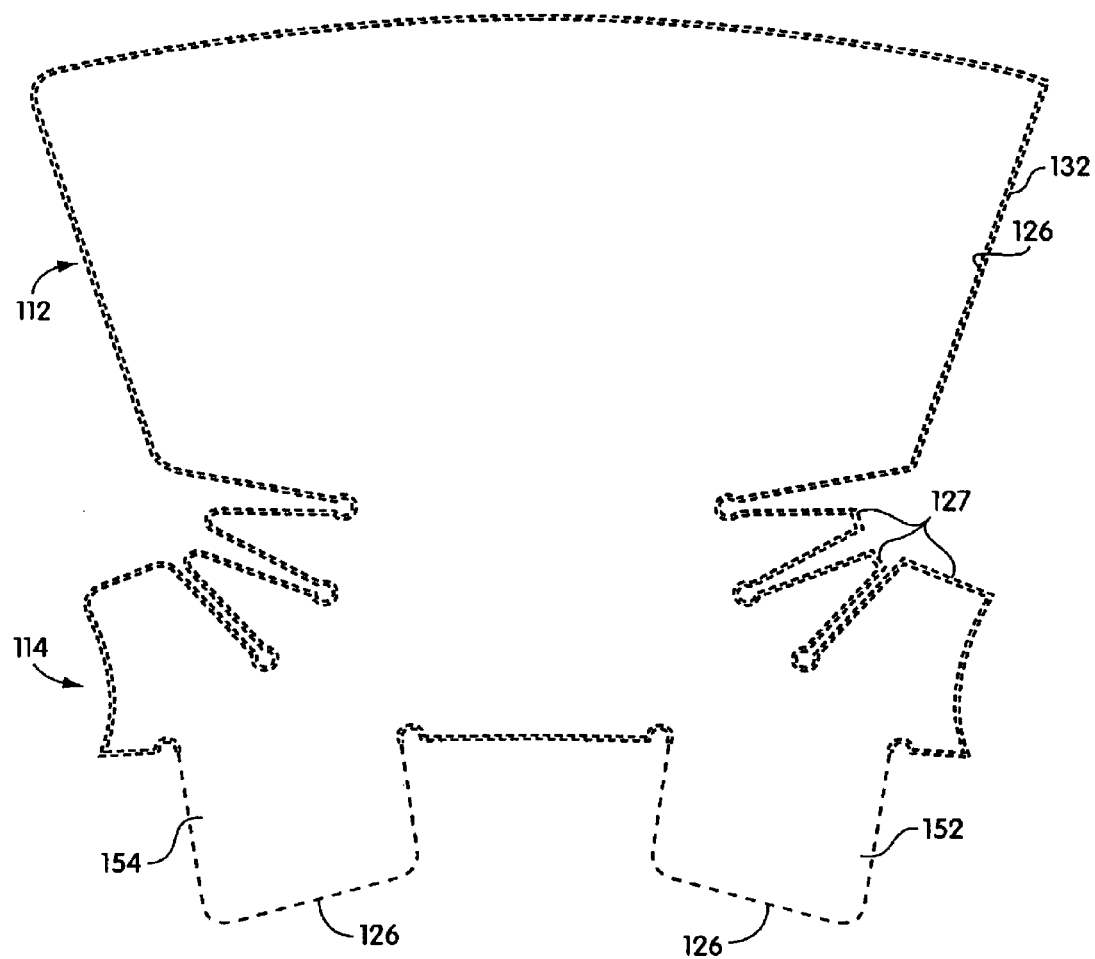
FIG. 12 is an illustration of a pattern for the bladder and shell of the therapeutic covering.
Figure 13:
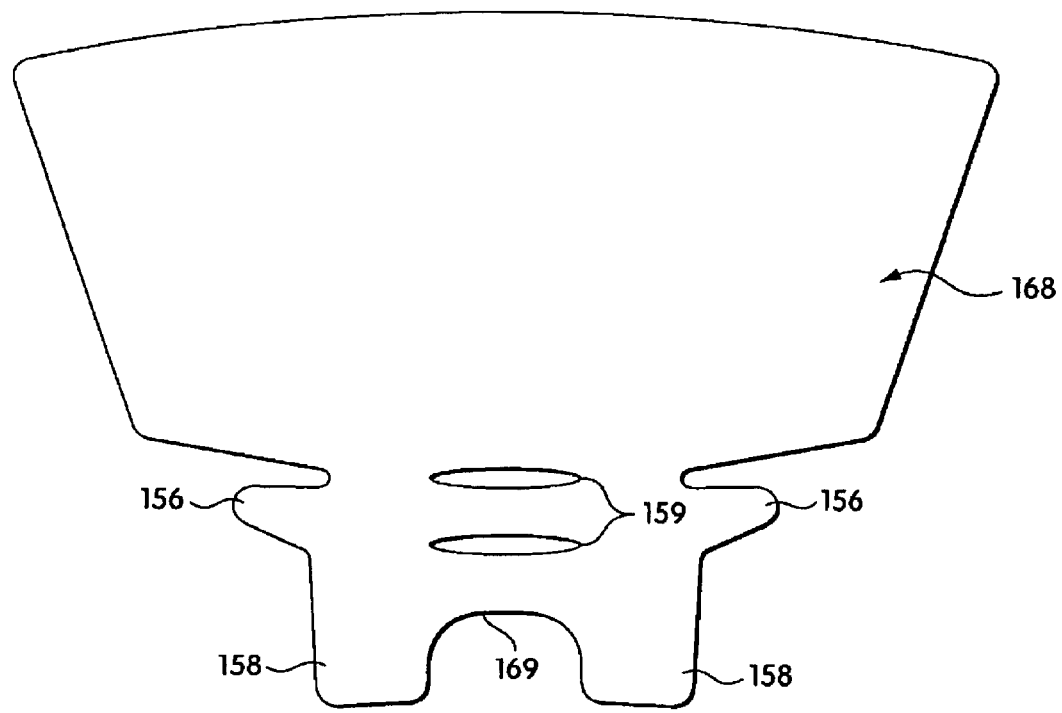
FIG. 13 is an illustration of a pattern for a single piece structural support.
Figure 14:
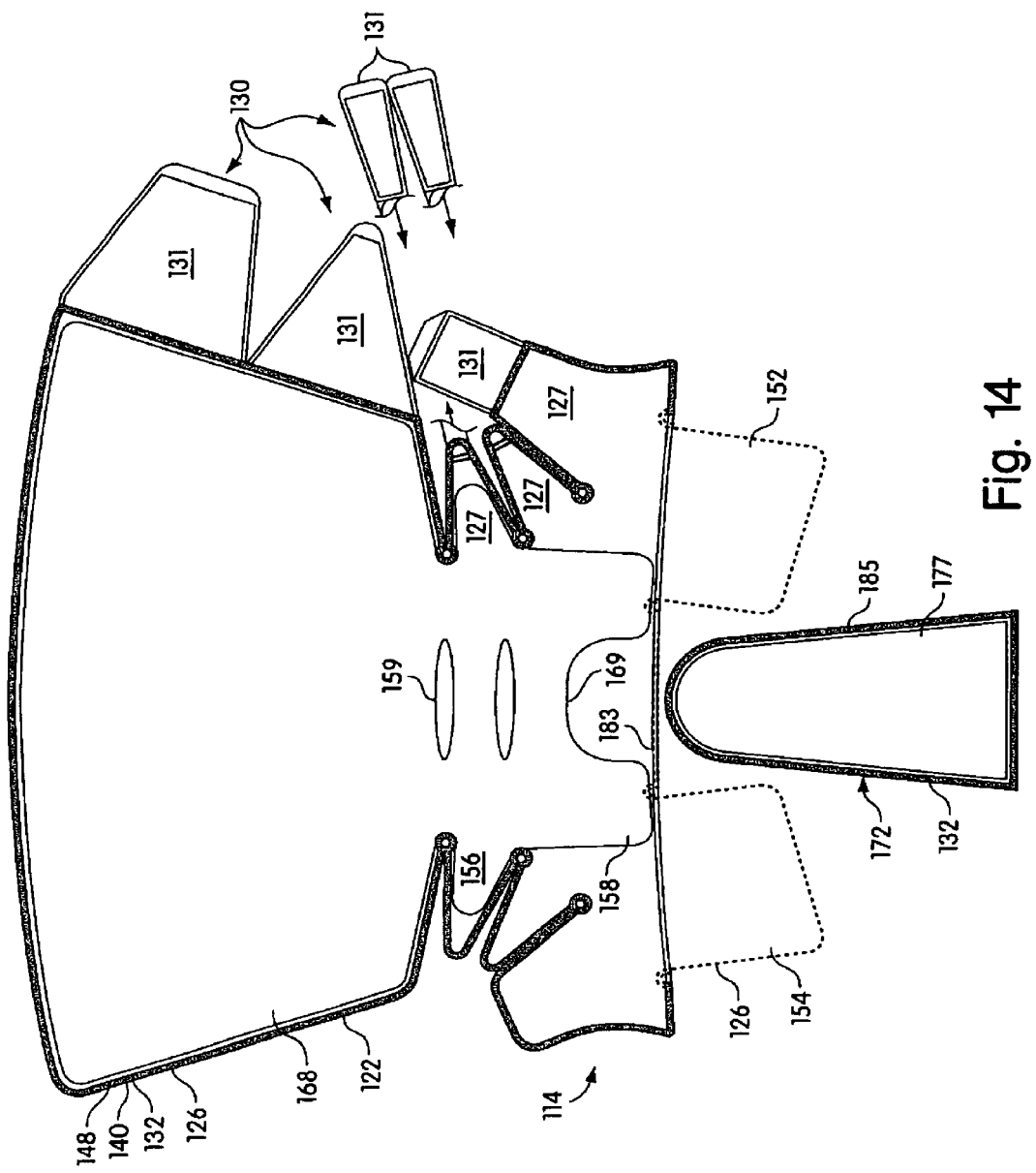
FIG. 14 is an illustration of the several patterns assembled together.

FIGS. 12–14 illustrate pattern shapes useful in forming the therapeutic covering 110. FIG. 12 shows a pattern for both the double wall bladder 126 and the shell 132. The shell 132 is represented by the outer-dashed line and the double wall bladder is represented by the inner-dashed line, both lines tracing a similar pattern. The double wall bladder pattern, though following the same shape as the shell pattern, is slightly smaller to provide a bonding area at the outer periphery 140 of the bladder walls to create a seam 148 that joins the bladder to the shell. As can be seen in FIG. 12, the patterns are substantially the same through the calf area 112 and foot portion 114, including defining the shape of flaps 127, that are ultimately used to secure the covering to a limb. One difference between the pattern shapes can be seen at the bottom of foot portion 114 where only the bladder defines left and right sole tabs 152 and 154. Identification of left and right sides corresponds to the perspective of a user wearing the covering. The sole tabs 152 and 154 comprise the same double wall bladder 126 that extends through the covering. The sole tabs are not covered by the shell material. In the final construction of the covering, the sole tabs will be folded upward from their position shown in FIG. 12 to reside horizontally on top of the sole portion 172 as is shown in FIG. 8 and as will be discussed further below.

Figure 13A:
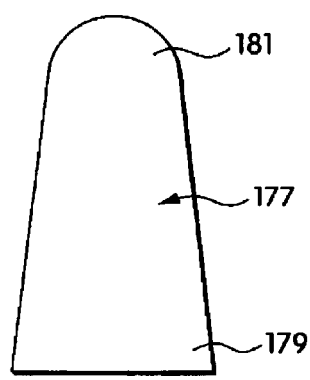
FIG. 13A is an illustration of a pattern for a sole insert of the therapeutic covering.

FIGS. 13 and 13A show patterns for both a structural support member 168 and the sole insert 177, both of which may be formed from closed-cell polymer foam material such as that discussed above. The structural support 168 shown in FIG. 13 is cut to substantially follow the pattern of the shell 132 shown in FIG. 12. However, the structural support need not follow the shell pattern in the more intricate areas of the flaps 127 because its primary function is to provide column support to the calf portion of the covering. The structural support is not needed in the flaps, which wrap over the top of the foot. However, wing extensions 156 which correspond with at least one series of flaps 127 of the outer wall 122 may be formed in the structural support 168 to help locate it and prevent it from sliding in its sandwiched position between the double wall bladder 126 and shell 132. As discussed previously, the structural support may be provided with an arch 169 that rises over the top of the heel to better accommodate this protruding portion of the foot. With the arch 169, two extension tabs 158 are defined on either side and serve to continue the structural support down to the base of the calf portion of the covering. To improve flexibility in the Achilles tendon area, several notches 159 may be cut out from the support material above the arch.

FIG. 13A shows a sole insert 177 that will reside in the sole portion 172 of the covering to provide a base that helps maintain the form of the covering and also serves to cushion the bottom of the users foot during ambulation. The sole insert 177 has a more narrow width at the heel area 181, which gradually widens along its length to a maximum width at the toe area 179 of the sole insert. However, it is noted that in the configuration of an open toe covering, as has been shown in the figures and descriptions, the toe area 179 will actually correspond to the ball of the foot of the user.

FIG. 14 shows the patterns discussed in connection with FIGS. 12–13 overlying each other as they would appear in the assembled covering. Additionally, the securement mechanism 130 is also shown. As mentioned above, the securement mechanism 130 may comprise Velcro hook portions 131 joined to flaps 127 that are formed in the outer layer 122. The outer periphery of the bladder 140 is bonded to the shell 132 of the outer layer 122 to form a seal 148 to secure the bladder to the covering. The structural support 168 is captured between the double wall bladder 126 and shell 132. Along the bottom of the covering, the sole tabs 152 and 154 extend from the bonded structure of the shell 132 and bladder 126. However, it is emphasized, that the sole tabs 152 and 154 are a continuation of the double wall bladder 126 and are open to the interior chamber of the bladder to be filled along with the bladder. To permit the sole tabs 152 and 154 to remain open to the remaining portion of the bladder 126, the seal 148 is discontinued along the portion of the covering that corresponds with the tabs. Additionally, the bladder may, but need not be, bonded to the shell 132 along the heel portion 183 of the covering, between the tabs 152 and 154. The sole 172 is formed as a separate component comprising the sole insert 177, which is covered by a layer of shell material 132 over its entire surface. The sole component 172 may then be bonded to the foot portion 114 of the covering along its edges 185. Before the sole portion 172 is bonded to the covering tabs 152, 154 are folded upward, so that after bonding, they may lie flat on top of the sole portion, overlapping each other, as is shown in FIGS. 8 and 15A and 15B.

Figure 15A:
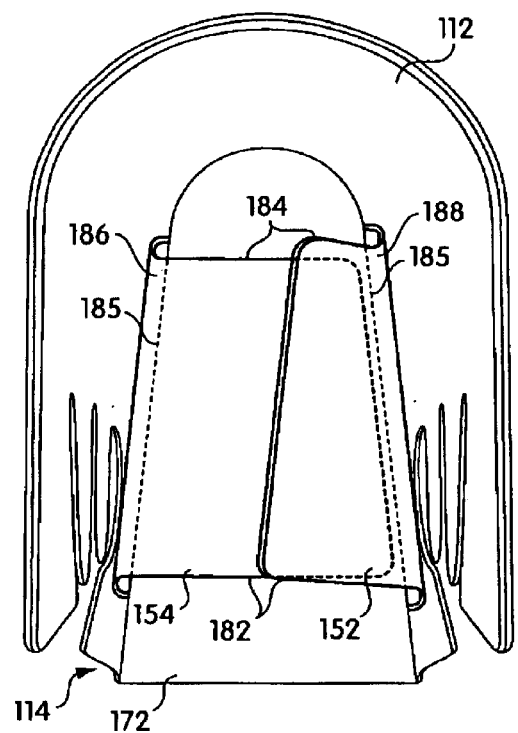
FIGS. 15A and 15B are top view illustrations of the sole portion of the therapeutic limb covering.
Figure 15B:
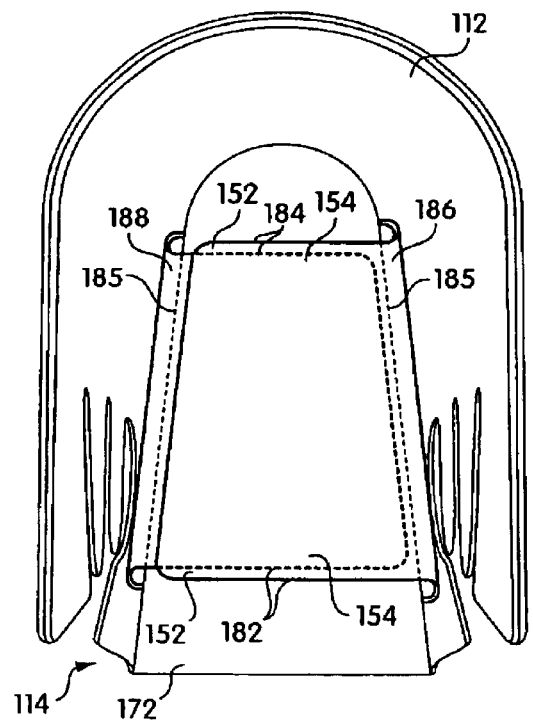

FIGS. 15A and 15B represent an overhead view of the sole portion 172 with the opening 128 of the covering 110 opened to permit viewing of the configuration of the sole area. As shown in FIG. 15A after the sole portion 172 has been bonded along its edges 185 to the foot portion 114 of the covering, the tabs 152 and 154 may be folded down to lie on top of the sole 172. FIG. 15A shows the right sole tab 154 being folded down onto the sole portion 172, first, prior to folding of the left sole tab 152. FIG. 15B shows the left sole tab 152 then being folded down on top of the right sole tab 154, both tabs thus lying horizontally on top of the sole 172. The tabs may be left free to fold up and down away from the sole, or may be secured to the sole by bonding. If secured, the sole tabs should be secured only at front and back edges 182 and 184. The sides of the sole tabs 186 and 188 should be left unbonded to permit communication between the tabs and the remainder of the bladder 126.

Figure 16:
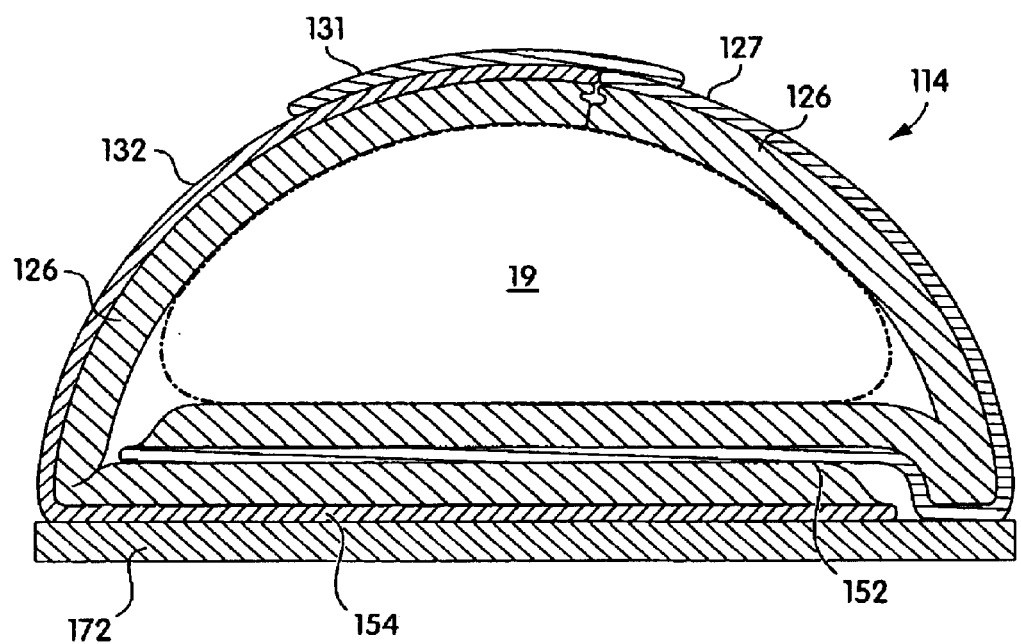
FIG. 16 is a sectional view of the foot portion of the therapeutic limb covering taken along the line 16—16 of FIG. 9.

FIG. 16 is a sectional view of the foot portion 114 taken along the line 16—16 of FIG. 9, but with the additional element of a user's foot 21 shown inside. The view shows that left and right sole tabs overlie each other and reside between the user's foot 19 and the sole portion 172. The bladder 126 surrounds the user's foot by its extension through left and right sole tabs 152 and 154 and by the overlapping securement achieved on top of the foot by flaps 127 being secured by hook portion 131 to shell 132 of the covering.

Figure 17:
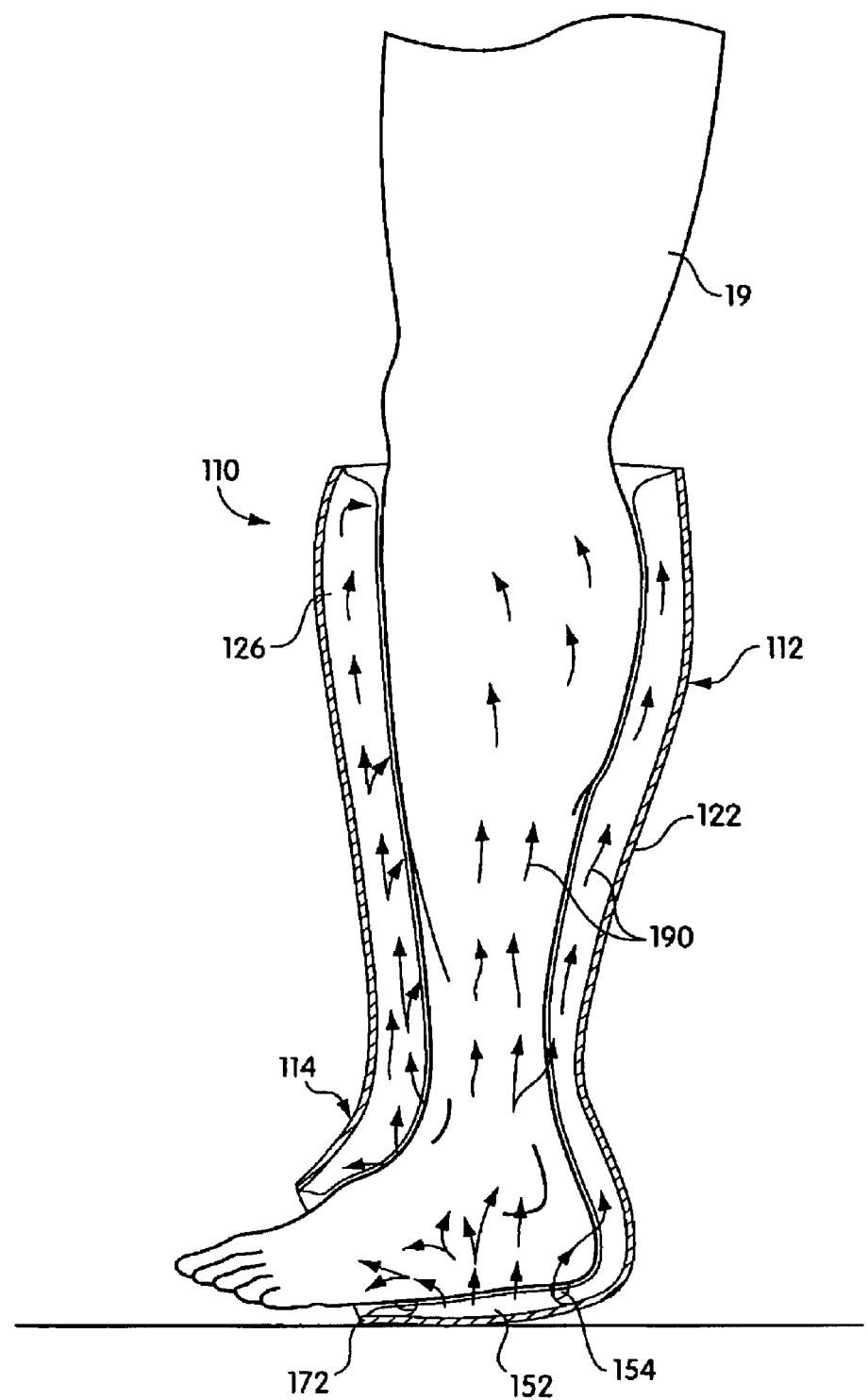
FIGS. 17 and 18 are side view, illustrations of the therapeutic limb covering showing liquid flow through the bladder.
Figure 18:
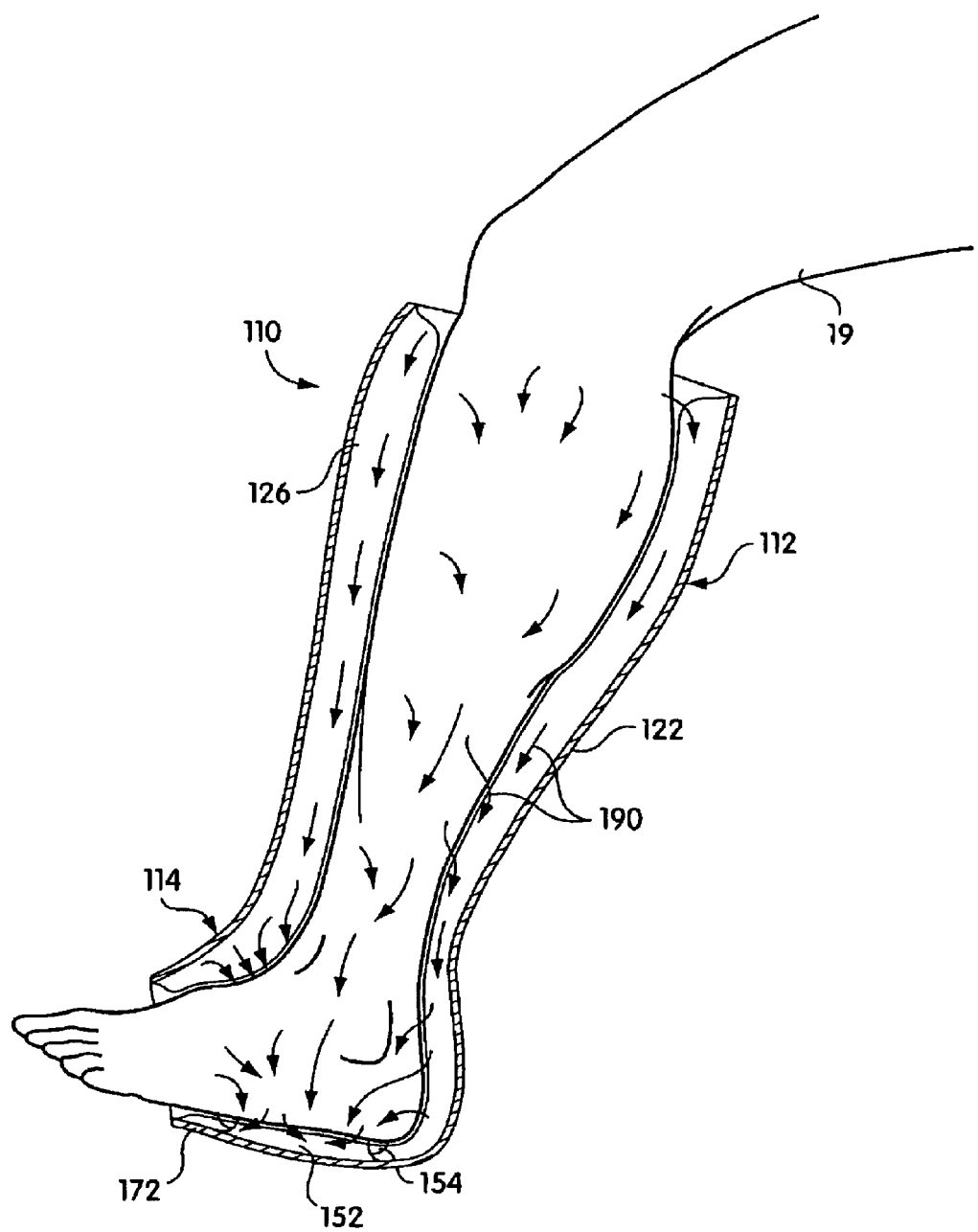

The arrangement of sole tabs 152 and 154 beneath the foot creates movement of the liquid contained in the bladder 126 during ambulation that is believed to improve the therapeutic benefit of the covering. As shown in FIGS. 17 and 18, a user wearing the covering 110 will compress and release the sole tabs 152 and 154 during ambulation that serves to compress and release this portion of the bladder 126 to cause movement of the liquid therein. In FIG. 17, the user is stepping down onto the sole 172 of the covering serving to compress the left and right sole tabs, reducing their volume and squeezing out liquid contained therein. Because the sole tabs define a continuation of the bladder 126 that extends around the side of the foot and beneath the sole of the foot, the liquid squeezed out of the tabs tends to be forced upward into the upper regions of the bladder 126 as indicated by flow arrows 190. The upward flow of the liquid is believed to help promote upward venous flow in the limb. FIG. 18 illustrates the flow of liquid when the user lifts the limb 19, as during ambulation, which serves to remove pressure from the left and right sole tabs 152 and 154. Without weight to bear on the sole tabs, the force of gravity on the liquid contained in the bladder 126 causes the tabs to quickly fill with liquid again. The filled left and right sole tabs are thus quickly made ready for the next step of the user so that another upward moving pressure wave can be created throughout the bladder 126 to promote the venous flow in the limb.

Figure 19:
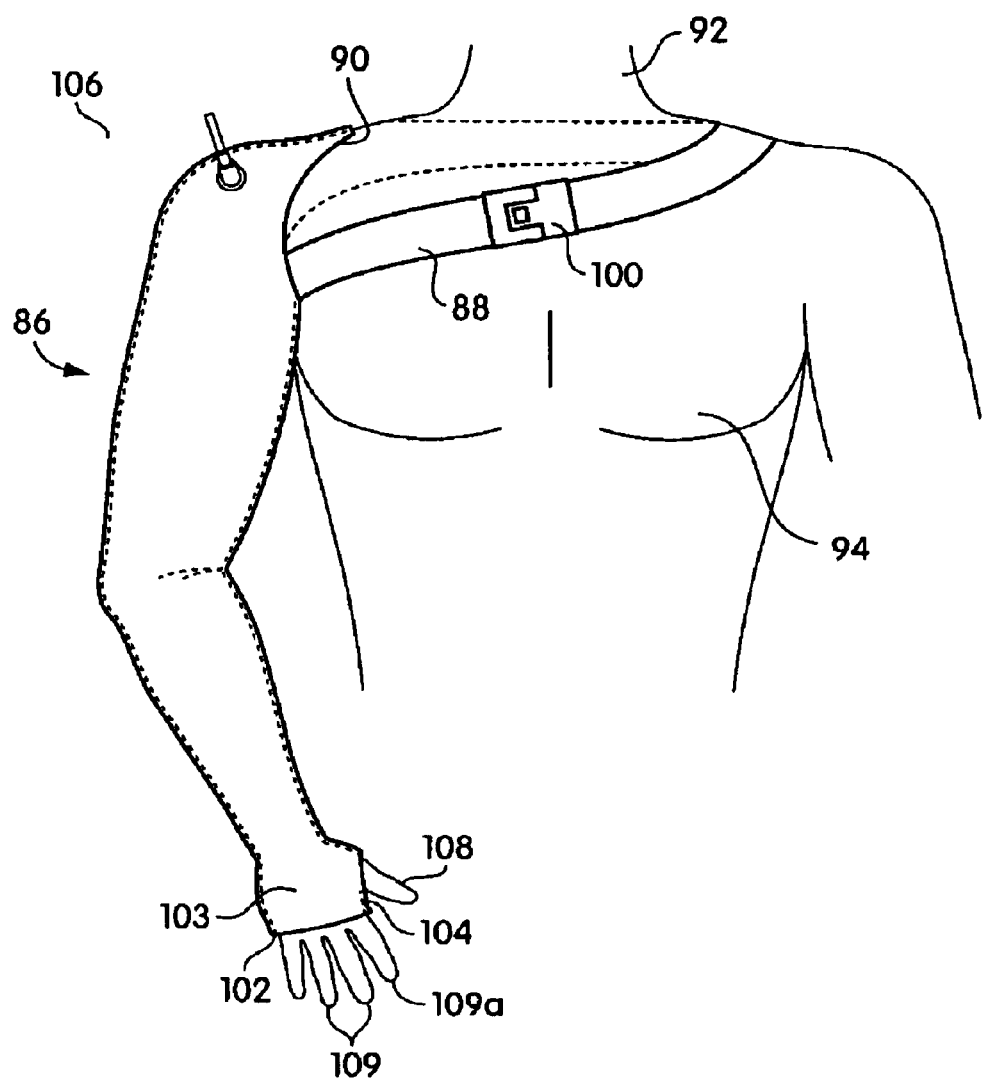
FIG. 19 is an illustration of a therapeutic limb covering configured to be worn about an arm.

FIG. 19 shows an embodiment of the limb covering configured to be worn about an arm. The arm covering 86 comprises a tubular sleeve of a length sufficient to cover the extent of the arm. The covering may be secured to the arm at the top by shoulder strap 88 having its ends joined to opposing sides of shoulder opening 90 of the covering. The strap extends around the patient's back (shown in phantom), loops around the neck 92 and opposite shoulder and extends back across the patient's chest 94 to the shoulder opening 90. To facilitate donning, a releasable buckle 100 may be provided on the strap to permit is detachment from the covering. Also the strap may be provided with a length adjustment to accommodate a variety of patient sizes. The arm covering is restrained from sliding up the arm by its gradual tapered shape as it drawn upward against the gradually increasing diameter of the arm. Additionally or alternatively the arm covering may be restrained at the hand opening 102 by a thumb loop 104 that comprises a tapered strap of covering material extending across the hand opening 102 and configured to fit between the thumb 108 and forefinger 109a of a patient's hand. The arm covering is otherwise configured in the same manner as the boot embodiment described above. The arm covering has a distensible inner layer and a non-distensible outer layer with a liquid tight bladder defined therebetween. A sealable port 106 in communication with the bladder is provided at the top of the arm covering. Materials and methods of fabricating are also the same as those used for the boot limb covering.

Figure 19A:
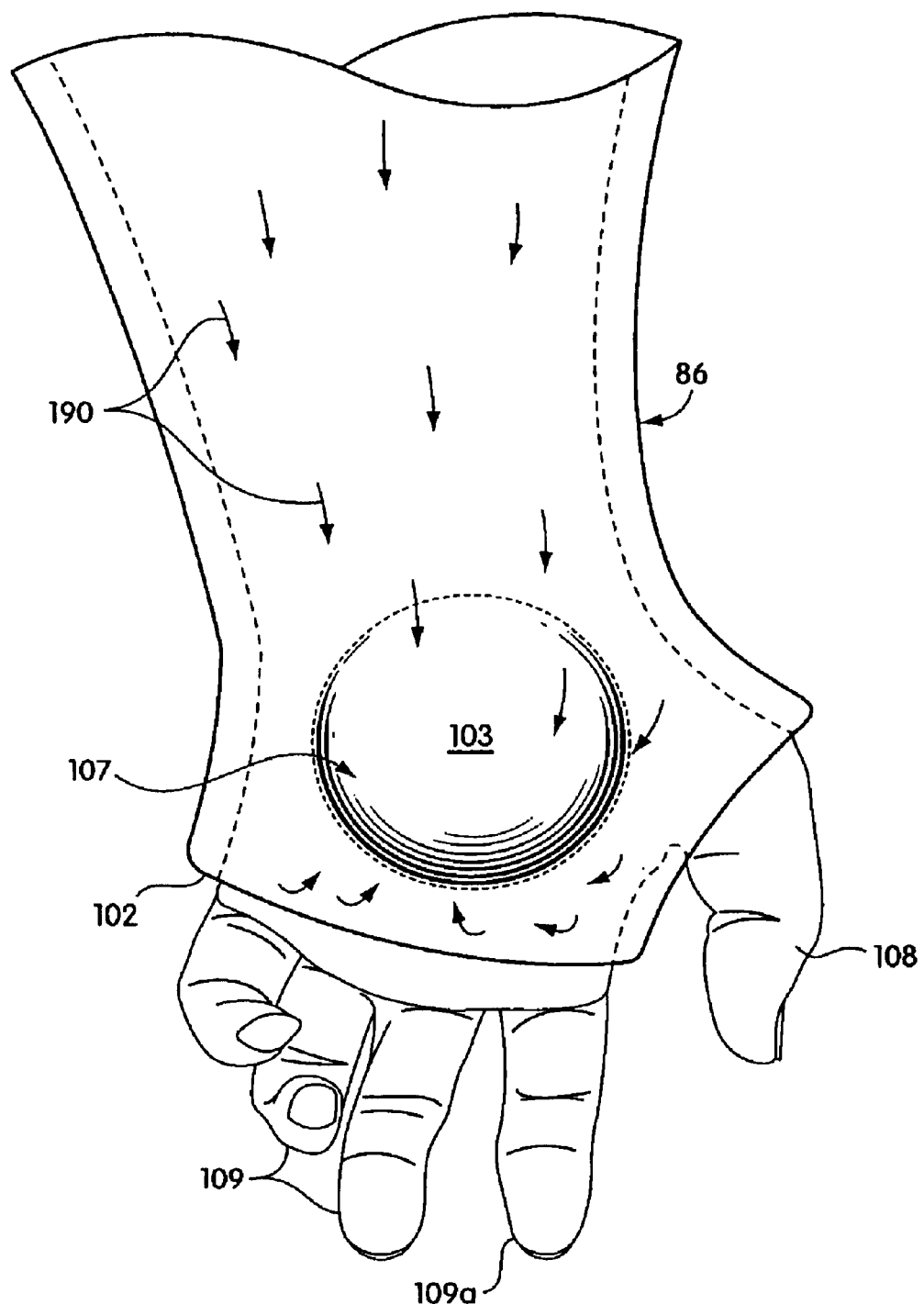
FIG. 19A is an illustration of a manual pump bulb area of a therapeutic limb covering configured to be worn about an arm.

To create alternating upward movement of the liquid through the arm covering for added therapeutic as described above in connection with the boot embodiments, a manual compression bulb area 103 may be integrated in the arm covering as shown in FIG. 19A. The manual compression area 103 (shown in phantom in FIG. 19) should lay comfortably in the palm 107 of the hand for compression by the user's fingers 109 and palm 107. The bulb should be in communication with the bladder of the device so that compression and expansion of the bulb volume results in pressure changes in the bladder that serve to urge liquid, to or away from the bulb. Preferably, the manual compression bulb area comprises an extension of the covering and its bladder to the palm area 107 of the hand, without additional specialized components. By compression and release of the bulb, the desired liquid movement can be achieved, as is demonstrated in FIG. 19A showing the flow 190 of liquid moving toward the user's palm upon release and expansion of the bulb area 103. Liquid flows downward to the palm under the force of gravity to fill the bladder area defined by the bulb 103. The filled bulb area is then ready for the next compression by the user's hand to drive the flow 190 of liquid up the arm.

In use, the patient places the limb covering around the limb 19 prior to filling it with liquid. In the case of a boot limb covering releasable securement mechanism 30 is released to open the limb covering to permit donning over a bare foot or stocking and foot. It is noted that the following description of use refers to the boot 10 for simplicity, but that it should be understood that the boot embodiment 110 is used in the same manner. After the covering is slipped on so that the foot portion 14 covers the foot of the user, the securement mechanism 30 may be secured to tighten the calf portion 12 about the calf of the user. If provided, size adjusters 31 or Velcro fasteners may be tightened to customize the fit of the covering. A loose fitting shoe may then be slipped over the foot portion 14 of the covering. Liquid may then be added to the bladder 26 of the covering 10 through valve 62.

Figure 20:
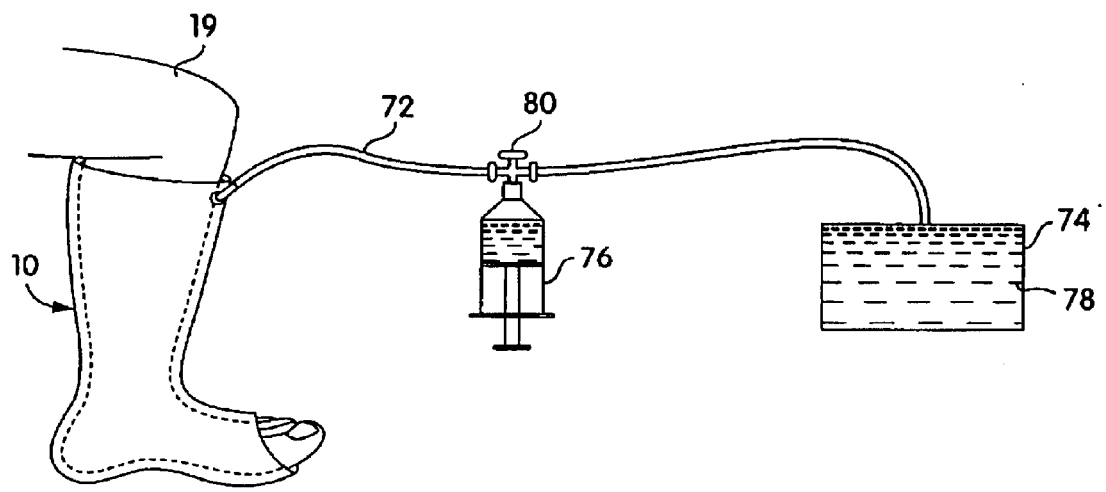
FIG. 20 is a diagrammatic illustration of components used in the filling process for the limb covering using a syringe.

As shown in FIG. 20, liquid is added through valve 62 to the boot 10 that has been placed on the limb 19. A liquid supply line 72 may be joined to the valve 62 by a lure type fitting or a quick connect type connection as discussed above. The liquid supply line 72 is in communication with a liquid reservoir 74 filled with any convenient liquid such as water 78. Liquid may be transferred from the reservoir 74 through the supply line 72 by pressure developed from a pump or a syringe 76. To facilitate use of the syringe, a three-way stopcock 80 may be used to join the syringe to the supply line 72. When the stopcock is closed to the boot but open to the syringe 76 and reservoir 74, a vacuum may be drawn by the syringe to fill it with liquid. Next, the stopcock is opened to the boot and syringe and closed to the reservoir so that the syringe may be pressurized to move the collected liquid into the boot. Liquid can be transferred to the boot until it appears full to the user or until a prescribed volume or pressure has been reached as measured using the syringe.

Figure 21:
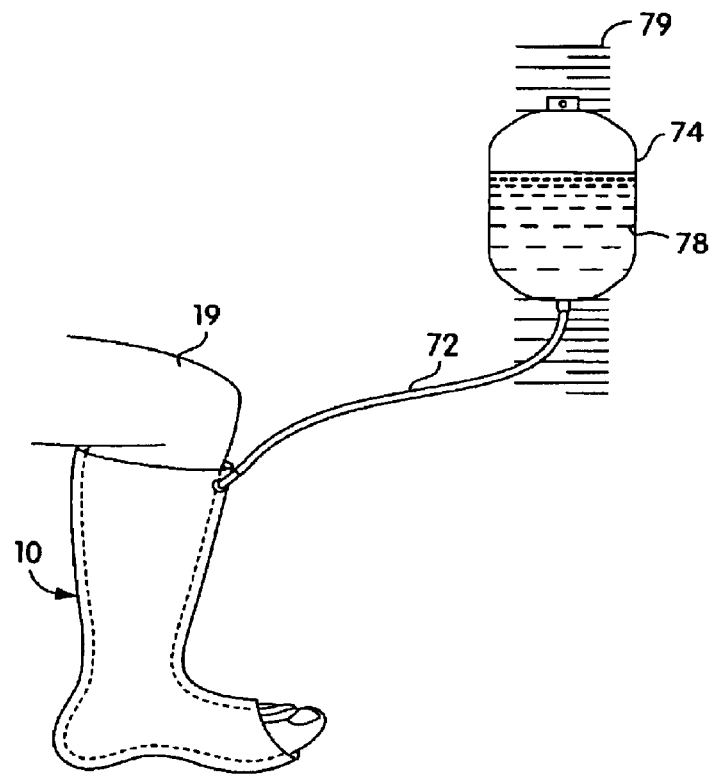
FIG. 21 is a diagrammatic illustration of the filling process of the limb covering using the force of gravity.

Alternatively, as shown in FIG. 21, liquid may be transferred from the reservoir 74 through supply line 72 to the boot 10 via the force of gravity. In this situation, the liquid reservoir, perhaps comprising a sealable bag, is elevated above the boot 10 to permit liquid to flow freely into the boot under the force of gravity. By this method, a pressure that has been clinically prescribed by a physician can be transferred by elevating the reservoir 74 to a measured height 79, known to correspond with a known pressure of liquid that will be dispensed from the reservoir to fill in the limb covering to a desired column height to deliver the needed pressure. Because the pressure applied to the limb by the present invention can be determined easily by measurement of the pressure of liquid that is transferred into the bladder, treatments can be prescribed more accurately by a physician and more accurately followed by the patient. In contrast, it is difficult to determine what pressure will be achieved with prior art wrapping materials because there effectiveness in applying pressure is highly dependent on the technique used by the one applying them.

An advantage of the hydrostatic pressure exerted by the limb covering is the linear increase in pressure that is applied at lower portions of the liquid column maintained in the covering. This characteristic of hydrostatic pressure is illustrated diagrammatically in FIG. 22 in which the boot 10 is shown with arrows 82 shown as graphical representations of the hydrostatic pressure forces exerted by the liquid column. The length of each arrow 82 relates directly to the magnitude of pressure force applied by the hydrostatic pressure of liquid contained in the limb covering at that point. Due to gravity, hydrostatic pressure forces increase linearly from the top of the covering to the bottom as is shown graphically by pressure profile line 83. However, pressure forces do not increase or decrease along a common horizontal plane, such as shown along foot portion 14.

It should also be recognized that the magnitude of force applied at a given point against the limb is not dependent on the volume of liquid maintained along the same horizontal plane extending from that point, but rather, hydrostatic force is solely dependent on and proportional to the height of the liquid column above it. The limb covering takes advantage of this effect by maintaining a thin liquid column around the limb and maintaining the height of the liquid column by its inelastic outer layer. Restraining the horizontal extent of the liquid in the bladder minimizes weight and to help maintain patient mobility without reducing the hydrostatic pressure applied to the limb.

Though the magnitude of force provided by hydrostatic pressure at any point along the limb is dependent on the height of the liquid column above that point, the total amount of force applied against the limb at any point can be increased by the amount of pre-charge pressure captured in the bladder during filling. The pre-charge pressure is created by over-filling the bladder with a volume of liquid that increases the pressure of the liquid above the pressure that is be created by hydrostatic effects alone. After the bladder is pressurized to have a pre-charge pressure during filling, sealing the port while maintaining the pressure in the liquid transfer line and bladder ensures that the pre-charge pressure will be maintained in the bladder.

In the situation discussed above in connection with FIG. 22, a volume of liquid is contained in the bladder sufficient only to provide force by hydrostatic pressure. The force applied at the top 87 of the covering is zero because the liquid column height does not extend beyond that point. FIG. 22A demonstrates the effect of adding to the bladder a volume of liquid sufficient to create a pressure pre-charge. The bladder containing the extra amount of liquid added to create the added pre-charged pressure may be considered to be "over-filled" in the sense that additional liquid has been added beyond what is required to fill the bladder to capacity with out creating extra pressure. As shown by pre-charge pressure profile line 85 in FIG. 22A, the pre-charge pressure supplements the hydrostatic pressure to increase the total magnitude of force applied to the limb at any given point. Thus the total pressure applied to the limb by the filled covering at any given point may be expressed as:

Total Pressure=Hydrostatic Pressure+Pre-charge Pressure

Figure 22:
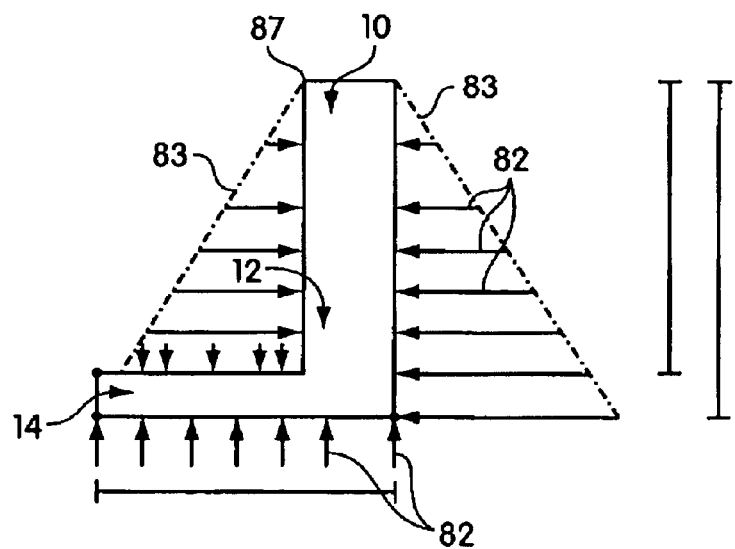
FIG. 22 is a diagrammatic illustration of hydrostatic forces applied to a limb while using the limb covering.
Figure 22A:
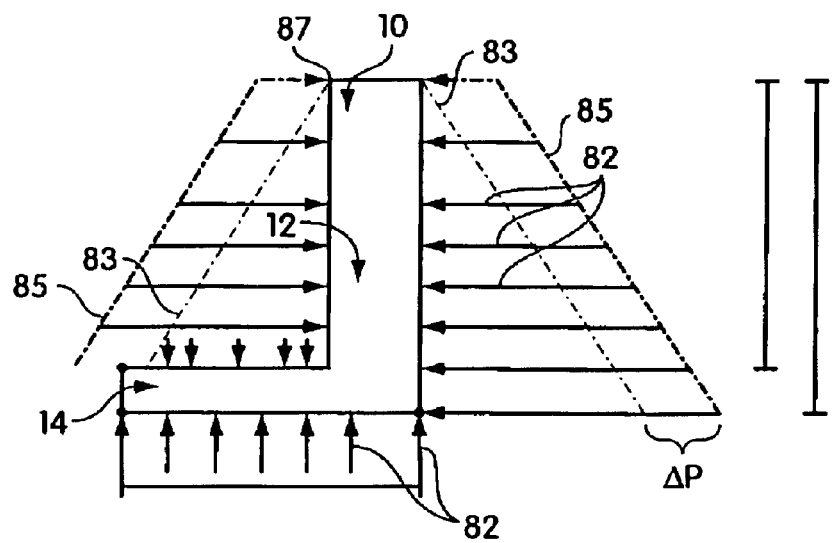
FIG. 22A is a diagrammatic illustration of hydrostatic forces applied to a limb while using the limb covering that has been pre-charged with additional liquid to achieve an over-fill condition.

Compared to the scenario shown in FIG. 22 the pressure at the top of the covering 87 of the pre-charged covering in FIG. 22A is not zero, but is equal to amount of pre-charge pressure that has been created. The amount of hydrostatic pressure at top 87 of the pre-charged covering is still zero, but because the total pressure at any point is the sum of pre-charge pressure plus hydrostatic pressure, the total pressure at the top 87 is equal to the pre-charge pressure. The pre-charge pressure value is constant throughout the bladder. The hydrostatic pressure at all other points in the covering of FIG. 22A having a pre-charge is increased by the constant amount of the pre-charge pressure. In FIG. 22A, the amount of pre-charge pressure is equal to the ΔP shown between the pressure profile 83 of hydrostatic pressure alone and the pressure profile 85 created in a covering that has been pre-charged with additional pressure.

It may be desirable to increase the pressure applied to the limb by adding a pre-charge pressure for certain treatments prescribed by a physician. If the bladder is filled with a syringe as described above, the pre-charge may be created by continuing to displace liquid volume with the syringe until the desired pre-charge pressure is achieved as measured at the at the top of the boot or at the syringe when it is maintained at the same height as the liquid transfer valve at the top of the boot. When filling the bladder to have a pre-charge pressure it should be understood that the pressure being measured at the port on the top of the covering does not include the hydrostatic pressure component that will exist at lower points in the bladder. If the bladder is filled by gravity feed as discussed in connection with FIG. 21, the liquid reservoir 74 may be elevated to a greater height to increase the magnitude of pressure experienced at the port 62 of the covering. A prescribed height 79 can be calculated with consideration of an appropriate pre-charge value. Alternatively, a pre-charge pressure can effectively be created after filling of the bladder by using adjusting straps 31 to tighten the covering about the limb and reduce the volume of the bladder.

Figure 23:
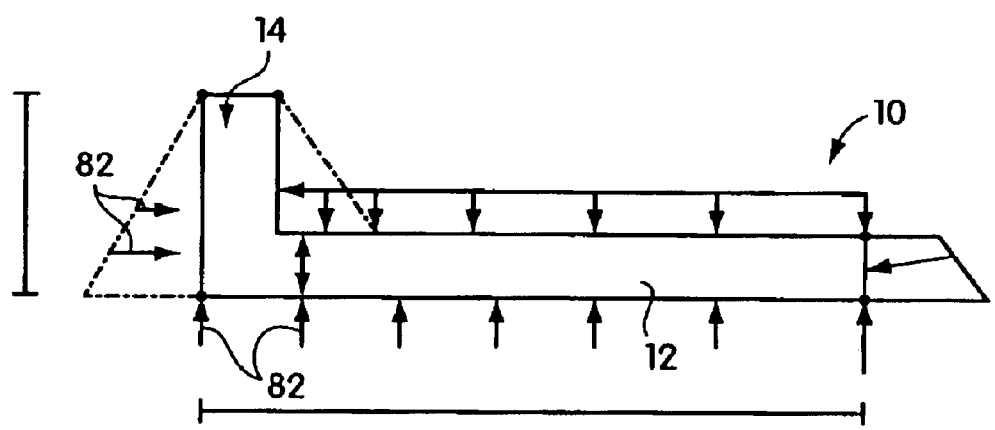
FIG. 23 is a diagrammatic illustration of hydrostatic forces applied to a limb while using the limb covering in a horizontal position.

FIG. 23 shows another diagrammatic illustration of hydrostatic forces as they exist in a boot limb covering, without a pre-charge pressure, oriented horizontally. The illustration mimics the circumstance when a patient may be lying in bed and the calf is oriented horizontally while the foot is arranged vertically. As with the previous diagram, it can be seen that forces applied to the limb do not change with position along the horizontal axis. Rather, the point forces increase linearly as point height decreases. Much of the limb that experienced high pressures in the vertical position shown in FIG. 22 now experience reduced pressure because the height of the liquid column maintained above those limb areas has been reduced. By this characteristic of hydrostatic pressure the present limb covering becomes a suitable therapy device for patients suffering from poor arterial perfusion. Those patients can treat chronic swelling with the therapeutic limb covering by maintaining their limb in a vertical orientation for a period of time, then alternately reorient their limb to a horizontal orientation to temporarily reduce pressure to the limb and allow blood to flow into the limb area. Because the device need not be removed or emptied to reduce pressure, alternatingly treating a limb with pressure then relieving the pressure becomes a practical treatment scheme for one with both chronic swelling and arterial perfusion problems.

Additionally, in the horizontal position, the hydrostatic pressure applied by the limb covering to the bottom of the calf 84 is beneficial to support the limb on a patient-supporting surface to avoid the incidence of pressure ulcers that may develop in a bedridden patient. It is noted that the hydrostatic forces and pressure profile line experienced in an arm covering with the arm positioned vertically and horizontally would be similar to those shown for the boot embodiment in FIGS. 22–23.

Figure 24:
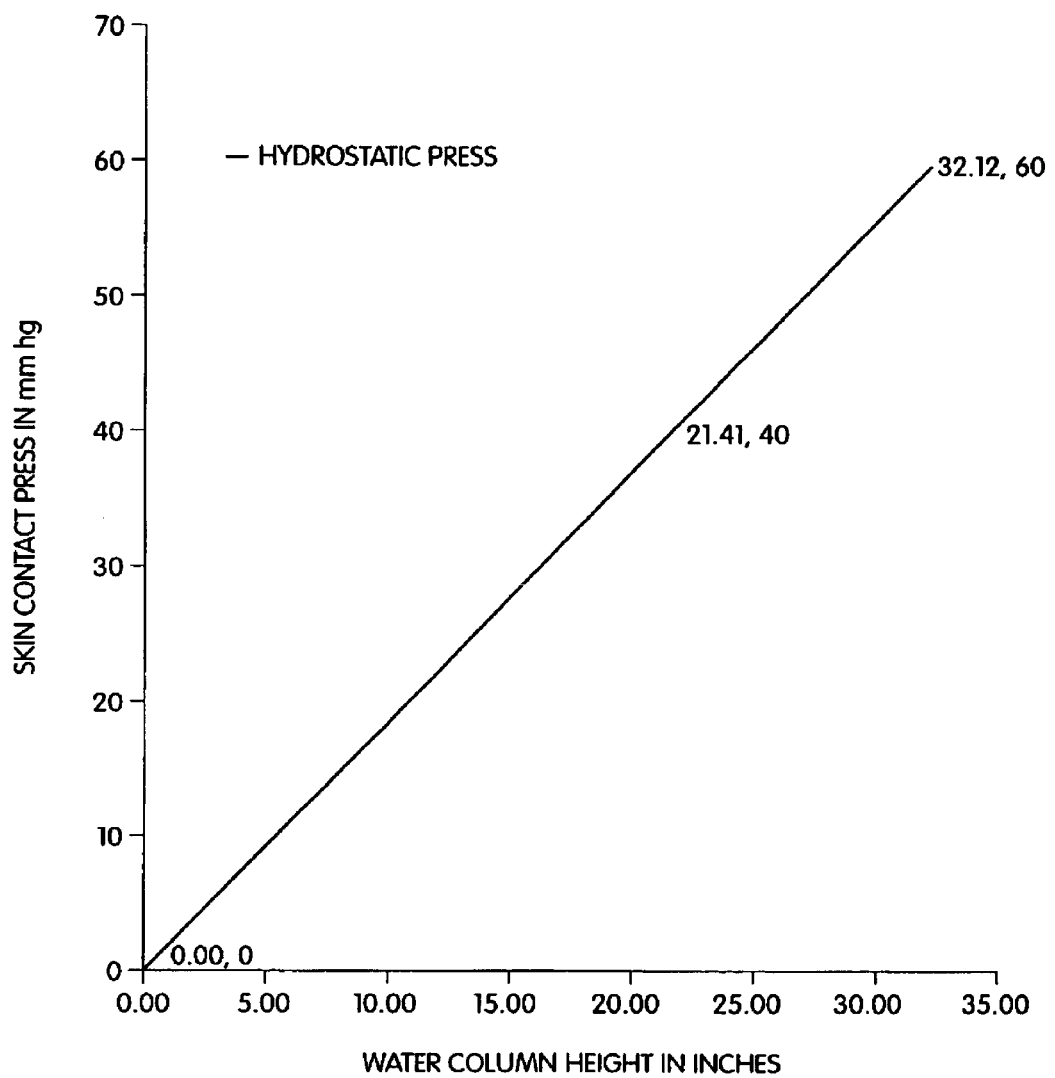
FIG. 24 is a graph plotting hydrostatic pressure in terms of skin contact pressure in millimeters of Hg versus water column height in inches.

FIG. 24 is a graphical representation of the linear increase in hydrostatic pressure as plotted in the skin contact pressure per water column height maintained in the limb covering.

It should be understood, however, that the foregoing description of the invention is intended merely to be illustrative thereof and that other modifications, embodiments and equivalents may be apparent to those skilled in the art without departing from its spirit.

Having thus described the invention what we desire to claim and secure by letters patent is:

1. A therapeutic limb covering for treatment of chronic swelling comprising:
    a substantially non-distensible shell having an inner surface;
    an elastic double-walled bladder joined to the inner surface of the shell, the bladder containing a liquid;
    a structural support between the bladder and the shell to resist collapse of the covering under the weight of the liquid in the bladder;
    wherein the double-walled bladder has an outer periphery along which the walls are bonded to each other and along which the bladder is bonded to the shell.

2. A therapeutic limb covering as defined in claim 1 wherein the bonds are formed by RF welding.

3. A therapeutic limb covering as defined in claim 1 wherein the bladder is configured to substantially surround a limb about which the limb covering is fitted.

4. A therapeutic limb covering as defined in claim 3 that is configured to be placed over a lower leg and foot of a patient with the shell and bladder extending from the bottom of the foot to approximately the top of the calf thereby surrounding substantially fully the lower leg.

5. A therapeutic limb covering as defined in claim 1 further comprising a filling port defined through the shell and communicating with the bladder.

6. A therapeutic limb covering as defined in claim 5 wherein the filling port comprises a valve with a quick connect fitting for receiving, in fluid communication, a line from a source of liquid.

7. A therapeutic limb covering as defined in claim 1 further comprising:
    a securable opening extending longitudinally along the covering to facilitate placement of the covering around the limb.

8. A therapeutic limb covering as defined in claim 7, further comprising at least one securement mechanism for altering the closeness of fit of the covering about the limb.

9. A therapeutic limb covering as defined in claim 1 wherein the structural support has a periphery that is substantially co-extensive with that of the shell.

10. A therapeutic limb covering as defined in claim 9 wherein the structural support comprises a sheet of flexible, semi-rigid material having sufficient compressive strength to prevent budding of the covering under weight of the liquid.

11. A therapeutic limb covering as defined in claim 10 wherein the structural support member comprises a sheet of polymeric closed cell foam.

12. A therapeutic limb covering as defined in claim 4 further comprising:
   the shell having a sole portion adapted to underlie the sole region of a patient's foot;
   the bladder having a sole portion thereof overlying the sole portion of the shell and located to be compressed under the influence of the weight of the patient when the patient's weight is applied to the sole portion of the bladder, the sole portion of the bladder being in communication with the other portions of the bladder thereby to transmit pressure from the sole portion of the bladder to the limb portion.

* * * * *